(12) United States Patent
Mohanty et al.

(10) Patent No.: US 12,702,291 B2
(45) Date of Patent: Aug. 11, 2026

(54) APPARATUS AND METHOD FOR MEASUREMENT OF FUNCTIONAL VISION IN PATIENTS WITH LOW VISION

(71) Applicant: Nanoscope Instruments, Inc., Bedford, TX (US)

(72) Inventors: Samarendra Kumar Mohanty, Southlake, TX (US); Sanghoon Kim, Bedford, TX (US); Michael Carlson, Rowlett, TX (US); Subrata Batabyal, Arlington, TX (US)

(73) Assignee: Nanoscope Instruments, Inc., Bedford, TX (US)

( * ) Notice: Subject to any disclaimer, the term of this patent is extended or adjusted under 35 U.S.C. 154(b) by 293 days.

(21) Appl. No.: 18/534,386

(22) Filed: Dec. 8, 2023

(65) Prior Publication Data

US 2024/0188817 A1 Jun. 13, 2024

Related U.S. Application Data

(60) Provisional application No. 63/386,644, filed on Dec. 8, 2022.

(51) Int. Cl.

| | |
|---|---|
| *A61B 3/032* | (2006.01) |
| *A61B 3/00* | (2006.01) |
| *A61B 3/113* | (2006.01) |
| *G06T 19/00* | (2011.01) |

(52) U.S. Cl.

CPC ............ *A61B 3/032* (2013.01); *A61B 3/0033* (2013.01); *A61B 3/0058* (2013.01); *A61B 3/113* (2013.01); *G06T 19/003* (2013.01); *G06T 19/006* (2013.01)

(58) Field of Classification Search

CPC ..... A61B 3/032; A61B 3/0033; A61B 3/0058; A61B 3/113; G06T 19/003; G06T 19/006

USPC .......................................................... 351/243

See application file for complete search history.

(56) References Cited

U.S. PATENT DOCUMENTS

2006/0143022 A1* 6/2006 Bird ....................... G06Q 10/10 705/2
2008/0192201 A1* 8/2008 Wengler ................. A61B 3/028 356/124
2010/0045934 A1* 2/2010 Neal .................. G01M 11/0257 351/246

(Continued)

FOREIGN PATENT DOCUMENTS

CN 115429213 A * 12/2022 ............... A61B 3/02
CN 115429213 A1 12/2022

(Continued)

OTHER PUBLICATIONS

International Search Report, corresponding PCT/US2023/083247, ISA/US May 24, 2024.

(Continued)

*Primary Examiner* — Mohammed A Hasan
(74) *Attorney, Agent, or Firm* — Wood, Phillips, Katz, Clark & Mortimer

(57) ABSTRACT

There is disclosed vision quantification systems and methods designed to evaluate functional vision. Specifically, the systems are designed with the intent to track a subject's vision using mobility and dexterity assessments. More specifically, at least one aspect of the invention relates to the design and application of the systems in the functional vision assessments in patients with low vision.

14 Claims, 21 Drawing Sheets

(56) References Cited

U.S. PATENT DOCUMENTS

| | | | | |
|---|---|---|---|---|
| 2012/0075586 | A1 | 3/2012 | Kirschen et al. | |
| 2012/0162606 | A1* | 6/2012 | Nakamura | A61B 3/032 351/221 |
| 2015/0116667 | A1* | 4/2015 | High | A61B 3/0041 351/243 |
| 2017/0319058 | A1 | 11/2017 | High et al. | |
| 2017/0360293 | A1* | 12/2017 | Novik | G09B 21/008 |
| 2019/0269315 | A1* | 9/2019 | Lu | G16H 50/20 |
| 2020/0345227 | A1 | 11/2020 | Bartlett et al. | |
| 2021/0398357 | A1 | 12/2021 | Samec et al. | |
| 2022/0261072 | A1 | 8/2022 | Altal et al. | |

FOREIGN PATENT DOCUMENTS

| | | | | |
|---|---|---|---|---|
| WO | PCT2021177968 | A1 | 9/2021 | |
| WO | PCT2022169748 | A1 | 8/2022 | |
| WO | WO-2022169748 | A1 * | 8/2022 | A61B 5/1128 |

OTHER PUBLICATIONS

Written Opinion of the International Searching Authority, corresponding PCT/US2023/083247, ISA/US May 24, 2024.

* cited by examiner

Fig. 1
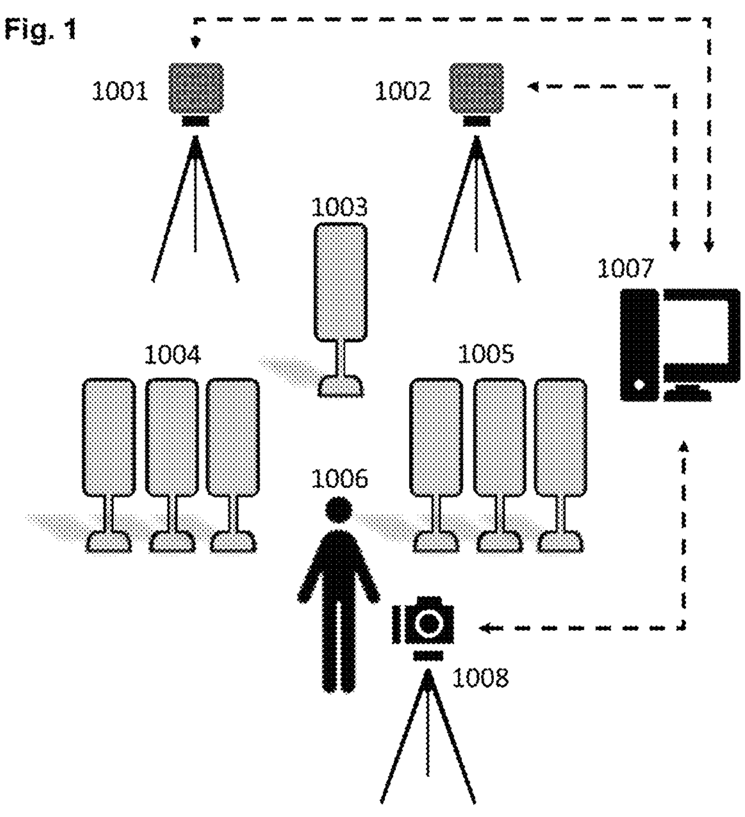
Fig. 2A
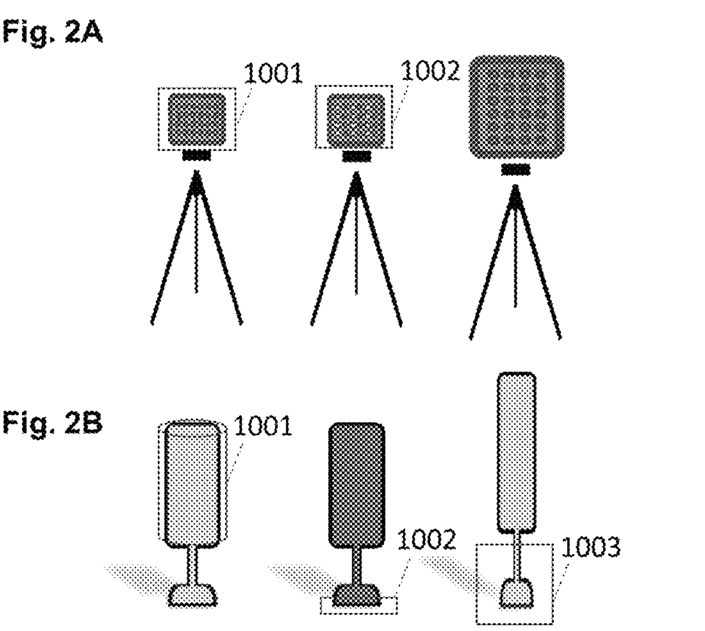
Fig. 2B
Fig. 2C

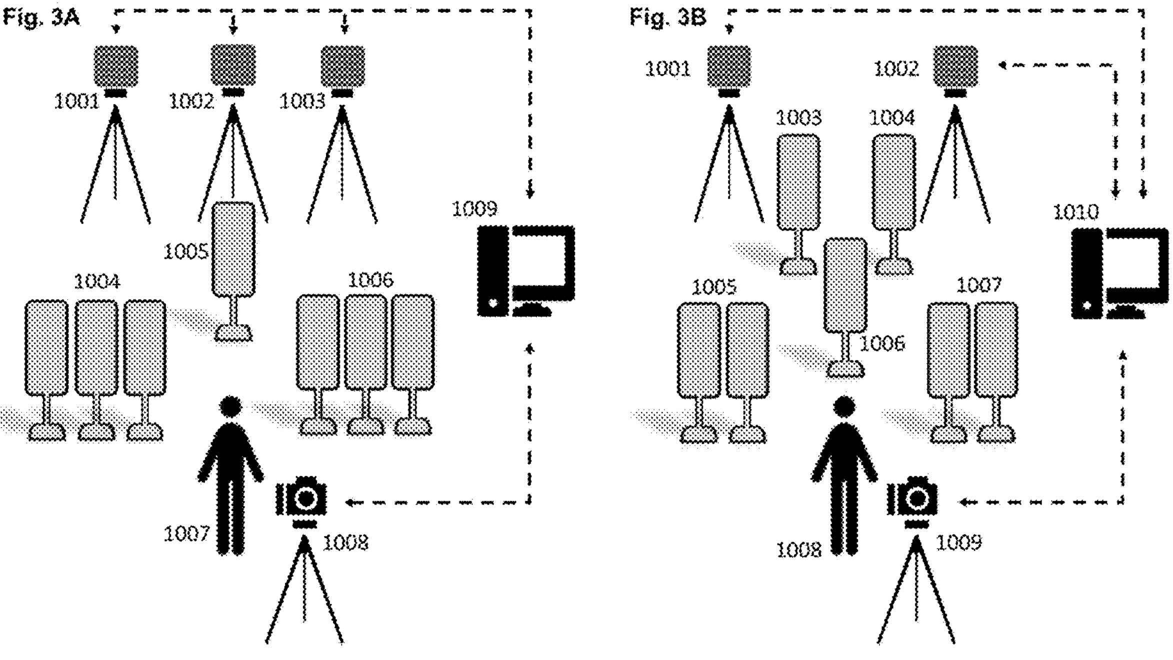
Fig. 3C
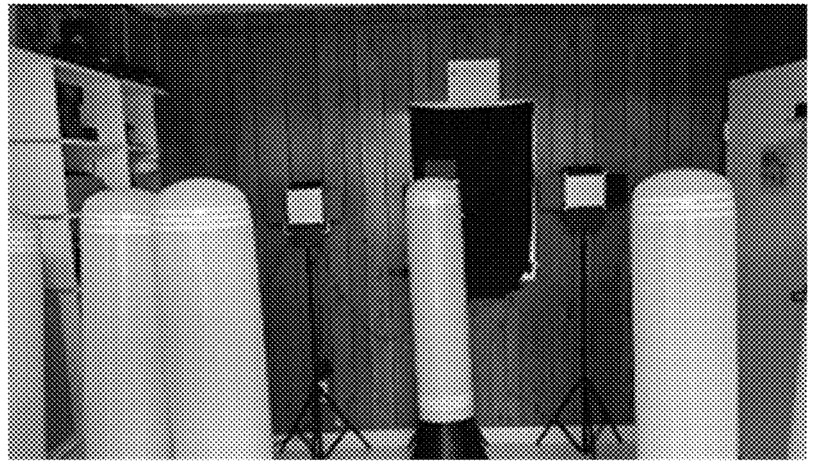

0.3
Y-Position (ft)
X-Position (ft)
Luminance (Lux)

1
Y-Position (ft)
X-Position (ft)
Luminance (Lux)

3
Y-Position (ft)
X-Position (ft)
Luminance (Lux)

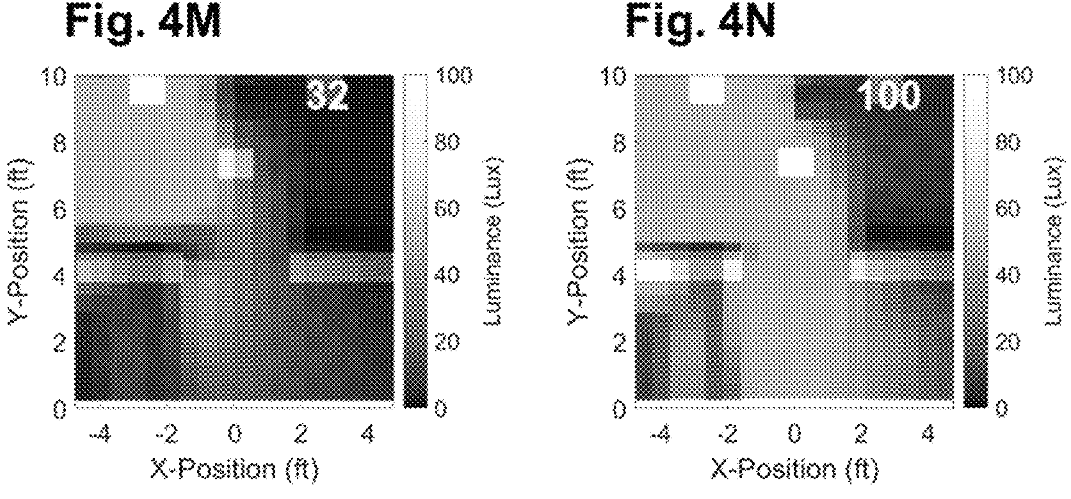
Fig. 5
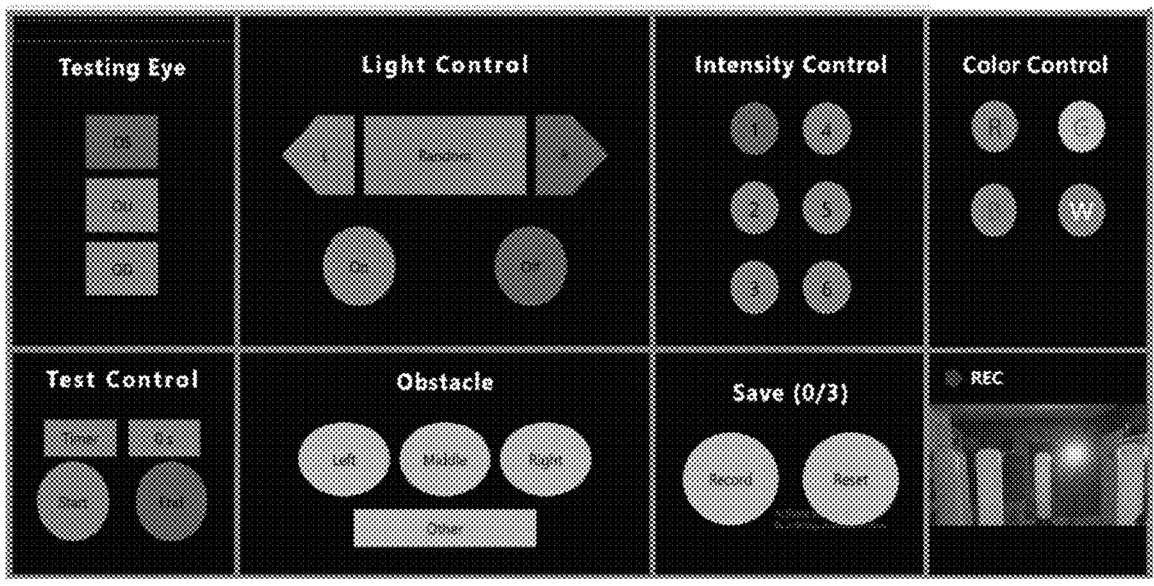

Fig. 6
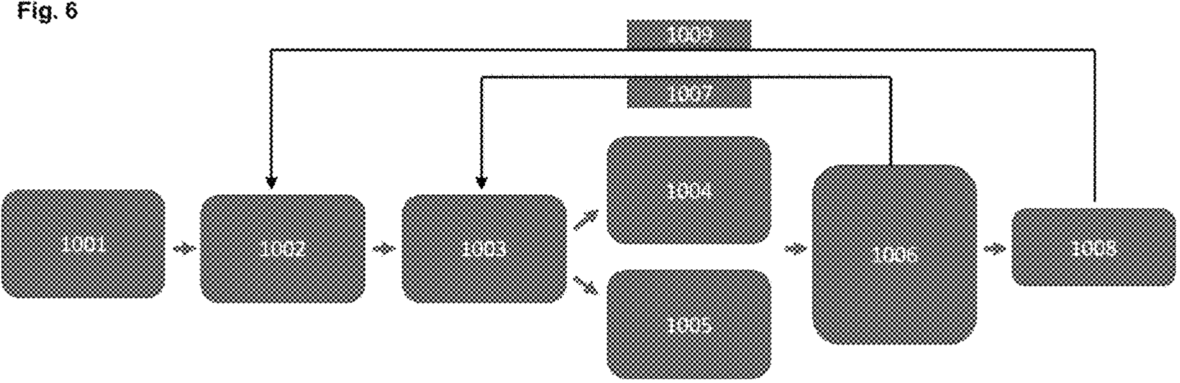
Fig. 7A
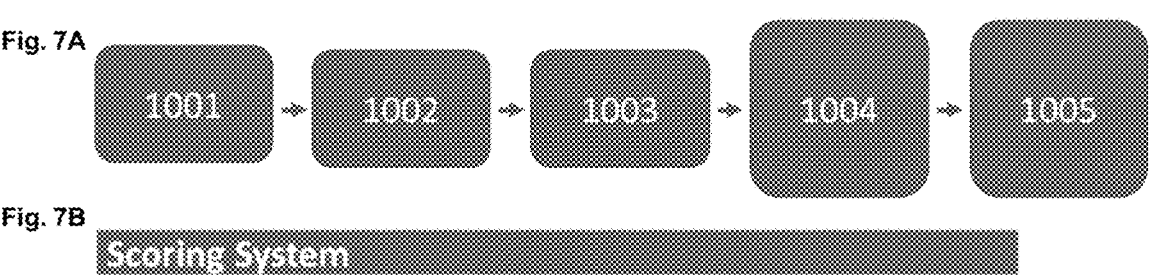
Fig. 7B
| Scoring System | |
|---|---|
| Score = - C1*N1 – C1*N2 – C3*N3 – C4*N4 – C5*N5 + 150*Screen Touch Score | |
| | |
| C1 = Left/right obstacle weight | N1 = number of left obstacle hit |
| C3 = Center obstacle weight | N2 = number of right obstacle hit |
| C4 = Tripod/wall weight | N3 = number of center obstacle hit |
| C5 = Repositioning weight | N4 = number of Tripod/wall hit |
| Screen Touch = 100, 0 if no screen touch | N5 = number of repositioning |
| | |
| Pass, if Score > X | |

1001
1002
1003
1004
1005
1006
1007
1008

1001
1002
1003
1004
1005
1006
1007
1008

Fig. 9A
Fig. 9B
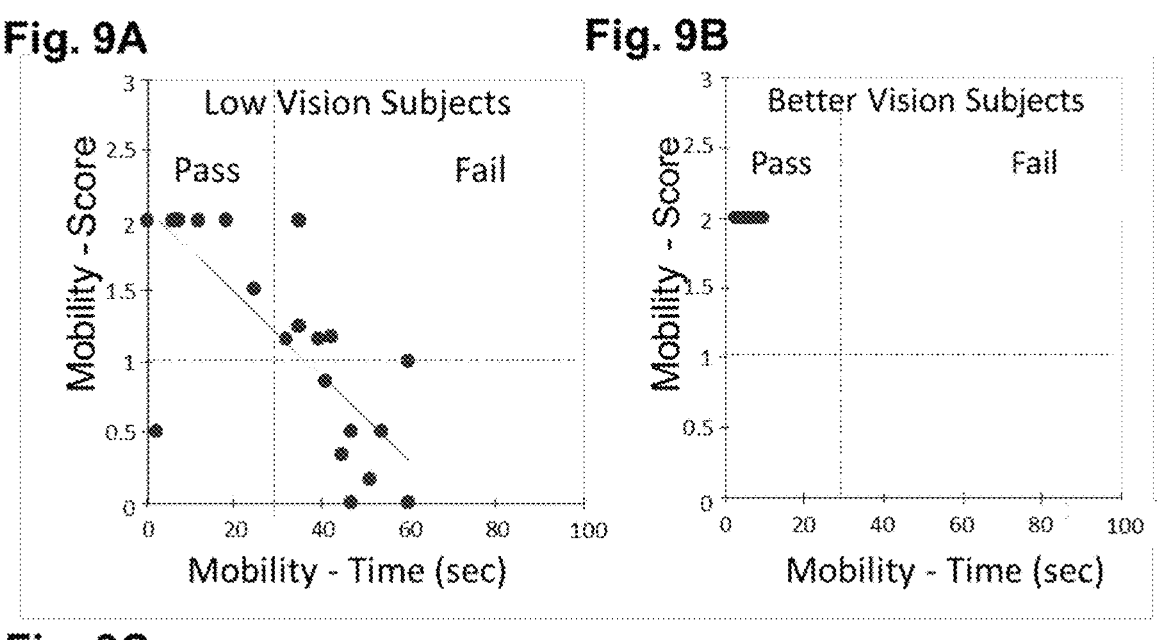
Fig. 9C
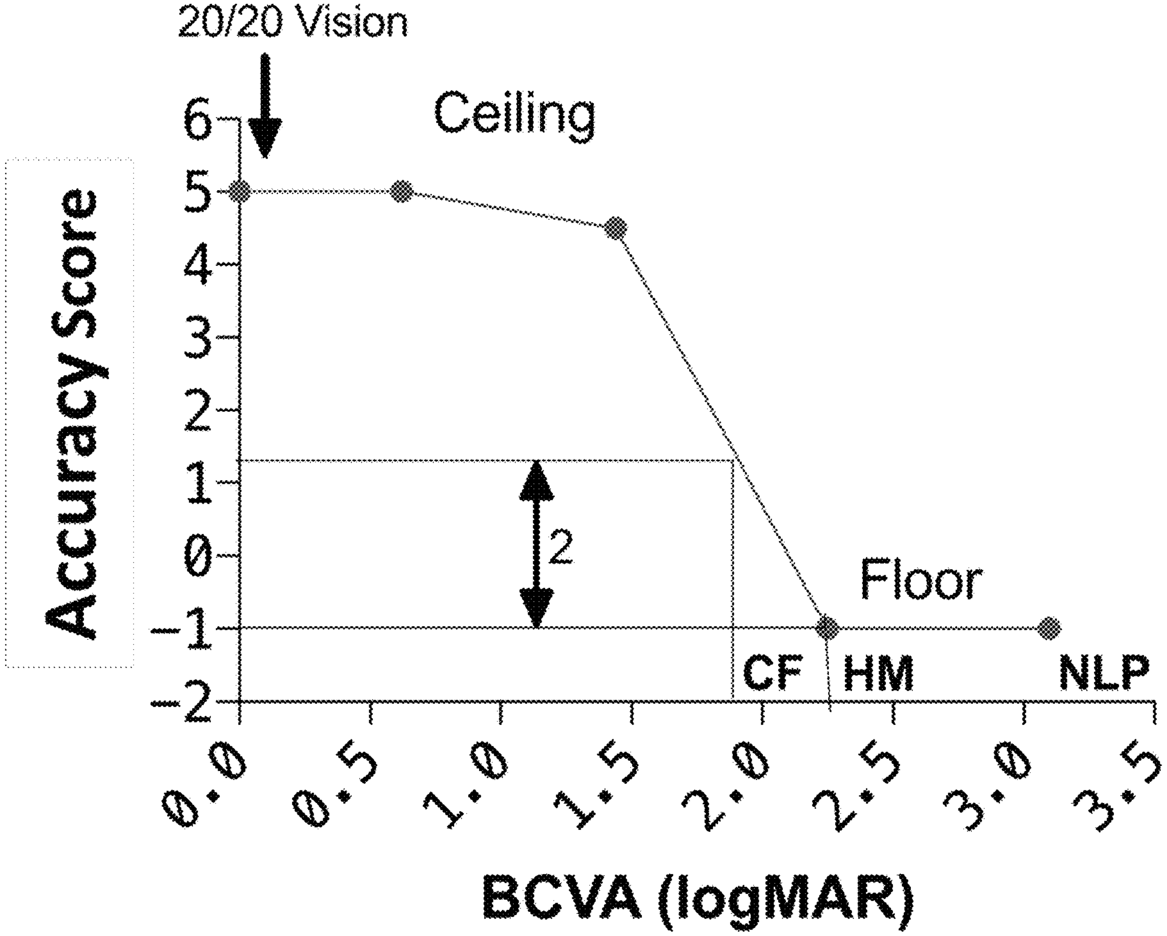

Fig. 12A

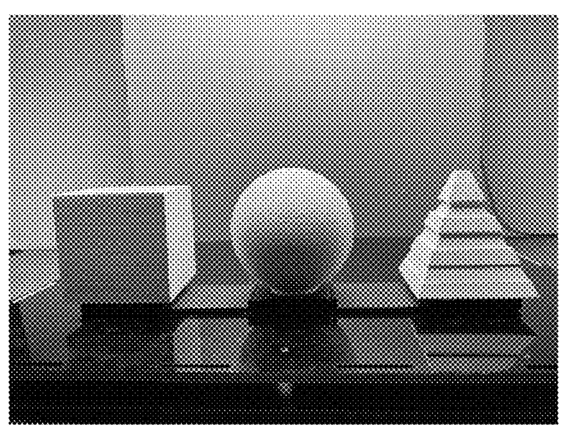

Fig. 12B

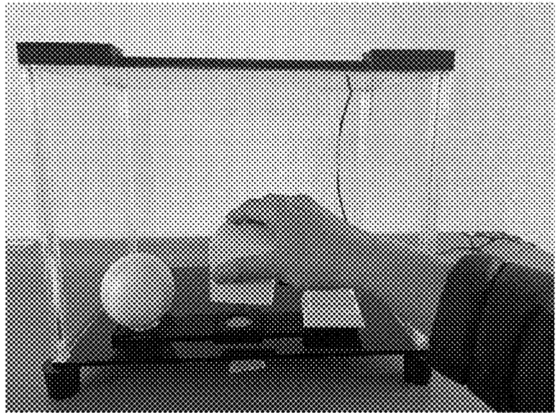

Fig. 12C

| Intensity (lux) | Shape Position 1 | Shape Position 2 | Shape Position 3 | Target | Shape | Selected | Correct? |
|---|---|---|---|---|---|---|---|
| 0.3 | Pyramid | Cube | Sphere | 1 | Pyramid | Sphere | no |
| 0.3 | Pyramid | Cube | Sphere | 1 | Pyramid | Nothing | no |
| 0.3 | Cube | Sphere | Pyramid | 3 | Pyramid | Pyramid | yes |
| 1 | Pyramid | Sphere | Cube | 1 | Pyramid | Cube | no |
| 1 | Pyramid | Cube | Sphere | 2 | Cube | Cube | yes |
| 1 | Cube | Pyramid | Sphere | 3 | Sphere | Sphere | yes |
| 3 | Pyramid | Cube | Sphere | 1 | Pyramid | Cube | no |
| 3 | Cube | Pyramid | Sphere | 3 | Sphere | Pyramid | no |

Fig. 13A

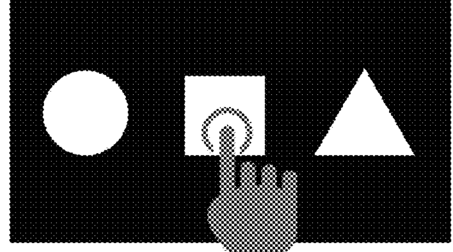

Fig. 13B

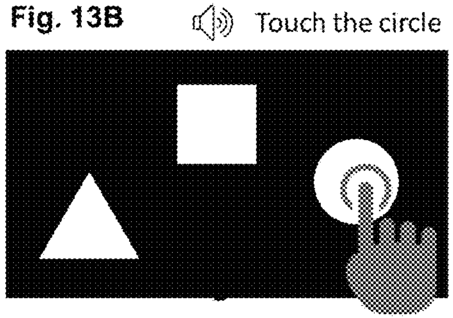

Fig. 13C

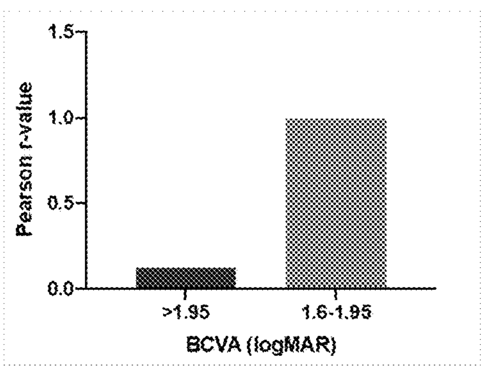

Fig. 13D

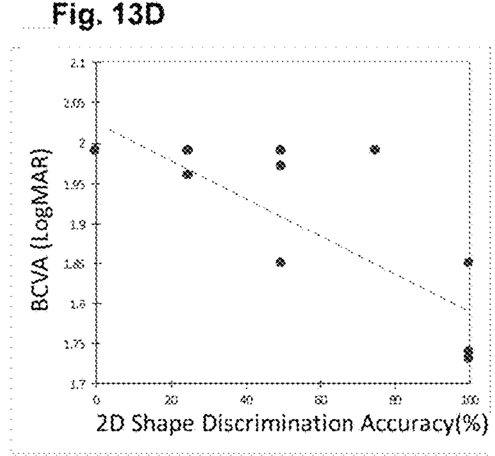

Fig. 13E

| Intensity (lux) | Shape Position 1 | Shape Position 2 | Shape Position 3 | Target Position | Target Shape | Target (X) | Target (Y) | Input (x) | Input (y) | Correct ? | Distance From target | Time(s) |
|---|---|---|---|---|---|---|---|---|---|---|---|---|
| 1 | Circle | Triangle | Square | 3 | Square | 1600 | 532.2 | 310.9 | 568.7 | no | 1079.0 | 1.03 |
| 1 | Circle | Square | Triangle | 2 | Square | 960 | 532.2 | 932.6 | 594.0 | yes | 0 | 1.09 |
| 1 | Square | Triangle | Circle | 2 | Triangle | 960 | 532.2 | 1617.5 | 558.1 | no | 484.3 | 0.87 |
| 3 | Circle | Square | Triangle | 3 | Triangle | 1600 | 532.2 | 217.4 | 685.4 | no | 1173.4 | 0.84 |
| 3 | Circle | Triangle | Square | 1 | Circle | 320 | 532.2 | 236.0 | 686.2 | yes | 0 | 1.00 |
| 3 | Triangle | Circle | Square | 2 | Circle | 960 | 532.2 | 236.5 | 686.8 | no | 529.2 | 2.35 |

Fig. 14A
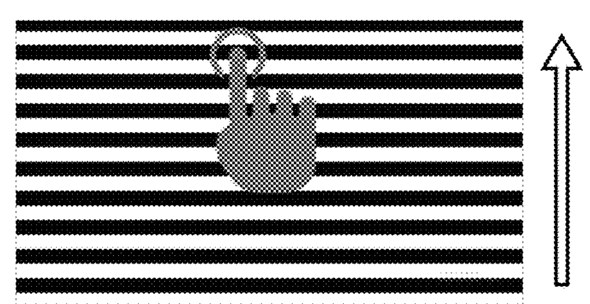
Fig. 14C
| Correct? | Flow Direction | Input (X) | Input (Y) | Time(s) |
|---|---|---|---|---|
| Correct | 1 | 245.29 | 705.60 | 1.34 |
| Correct | 4 | 384.71 | 670.87 | 1.05 |
| InCorrect | 3 | 310.91 | 687.93 | 0.26 |
| Correct | 1 | 366.69 | 725.83 | 0.14 |
| InCorrect | 3 | 221.31 | 792.98 | 0.32 |
| InCorrect | 2 | 280.35 | 882.68 | 0.18 |
| Correct | 4 | 218.51 | 952.11 | 0.21 |
| InCorrect | 2 | 257.05 | 1020.41 | 0.19 |
| InCorrect | 2 | 149.51 | 1015.33 | 0.15 |
| InCorrect | 3 | 466.92 | 890.08 | 0.74 |
| Correct | 4 | 423.56 | 1025.98 | 0.14 |
| Correct | 1 | 493.13 | 1013.12 | 0.24 |

APPARATUS AND METHOD FOR MEASUREMENT OF FUNCTIONAL VISION IN PATIENTS WITH LOW VISION

CROSS-REFERENCE AND PRIORITY

Some references, which may include publications, patents, and patent applications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference were individually incorporated by reference. This application claims the benefit of priority to U.S. Provisional application No. 63/386,644, filed Dec. 8, 2022, entitled "APPARATUS AND METHOD FOR MEASUREMENT OF FUNCTIONAL VISION IN PATIENTS WITH LOW VISION", which is hereby incorporated by reference in its entirety.

STATEMENT REGARDING FEDERALLY SPONSORED RESEARCH OR DEVELOPMENT

This invention was made with funding by Nanoscope Instruments, Inc. The Government has no rights in the invention.

FIELD OF INVENTION

The present invention relates to vision quantification systems and methods designed to evaluate functional vision. Specifically, the systems are designed with the intent to track a user's vision using mobility assessments, shape and optical flow recognition devices. More specifically, the invention relates to the design and application of the systems in the functional vision assessments in low vision patients.

BACKGROUND OF INVENTION

In case of visual impairment an evaluation of functional vision characterization is necessary to complete the assessment of an individual's vision-related abilities. In other words, functional vision is defined by how a person's vision is used in everyday activities.

The assessment of functional vision is characterized by measurement of multiple and varying parameters captured under complex, real-life conditions.

Visual disorders lead not only to physical impairment, but have a significant emotional and psychological impact on quality of life of the patients as well as family members. Types of loss of vision is varied from central to peripheral loss, reduced contrast sensitivity and night blindness. Though there exists number of devices such as Full-Field Stimulus Threshold (FST), Electroretinography (ERG)[1], Humphrey Visual Field[2] (HVF) to measure visual function in low-vision subjects, individually, these methods provide measure of single-parameter (e.g. intensity threshold in FST). Further, it is unclear if these existing tests measure a clinically meaningful outcome, and therefore, not widely accepted as a primary efficacy endpoint for low-vision studies.

Therefore, there is a need for development of a systems measuring the functional vision outcomes in the low vision treatment modalities. With the increase in regenerative medicine, especially gene and cell therapy, targeting different cell types to halt degeneration, refunctionalize cells or integrate new cells, assessment of functional vision of different and novel parameters for very low vision subjects is becoming increasingly important. Without being able to accurately measure the change in vision before and after treatment, it is not possible to fully assess the effect of treatment. The present invention intends to address and/or overcome the limitations discussed above by presenting new designs and methods not hitherto contemplated nor possible by known constructions.

SUMMARY OF THE INVENTION

The functional vision in low-vision subjects, especially inherited retinal disorders or glaucoma, degrades over time due to progressive loss of retinal cells or their function. The rate of decay in vision varies depending on the genetic mutation(s) causing the disease phenotype. Hereditary degenerations of the human retina are genetically heterogeneous, with well over 100 genes implicated so far for a single disease such as Retinitis Pigmentosa (RP). RP can be inherited as an autosomal-dominant (about 30-40% of cases), autosomal-recessive (50-60%), or X-linked (5-15%) trait[3]. However, there is a lack of objective reliable measurements in low-vision patients (with VA worse than 20/200 or 20/800 for example) due to non-availability of appropriate tool. Further, some diseases are bilateral while others affect more in one eye. Genetic variation may impact a subject's response to study intervention, susceptibility to, and severity and progression of disease. Therefore, longitudinal measurements of functional vision in the low-vision patients[4] are needed to establish natural history and evaluate therapeutic efficacy of cell/gene therapies.

The present invention provides a device and method for assessing functional vision in low vision patients, mimicking daily activities at varying light intensities such as walking toward lighted window or doorway avoiding obstacles as well as picking up objects on a table. A normal vision or better vision subject is expected to perform all the low vision tests without difficulty.

According to an aspect, the present invention encompasses a method of evaluating functional vision in low vision subjects (which may be worse than 20/200 for instance) comprising at least one of the steps of:

(i) conducting a Visually Guided Mobility Test comprising a single or multiple Light panel(s) for emitting light at different intensity levels or a lighted object(s) at different intensity; providing a single or multiple randomly-selected starting point(s) for a subject to find at least one of the Light panel(s) that is emitting light; providing a variable number of obstacle(s) positioned at different locations in the path to the Light panel(s) or the lighted object(s) to assess the ability of the subject to avoid them; providing at least one video camera for recording the mobility of the subject; providing a computer for switching at least one of the Light panel(s) or light shining on the object(s) ON/OFF, and varying the Light panel(s) light intensity or intensity of light shining on the object(s) and color by integrated software for directing and recording the performance of the Visually Guided Mobility Test; wherein the ability of the subject to detect and freely navigate towards the at least one of the Light panel(s) that is emitting light or lighted object(s) and avoid the obstacles is evaluated, without any other visual cues for direction; conducting a Visually guided Dexterity Test comprising a pre-calibrated Light panel for controlled illumination;

providing differently shaped three-dimensional (3D) objects that are stationary or moving; lighting the objects by the Light panel; detecting when the objects are placed or displaced; providing a control board communicating with a computer for controlling the light intensity levels of the Light panel; providing integrated software for providing instructions to the subject in a randomized order and for recording the performance of the subject; wherein the Visually guided Dexterity Test evaluates the ability of a subject to detect and discriminate an object and/or motion a collection from of differently sized/shaped/colored stationary/moving objects for near vision evaluation in three-dimensions; and/or (iii) conducting a Visually Guided Dexterity Test comprising multiple types of shapes being displayed at different intensity levels on a screen or Light panel in randomized order, wherein the Visually Guided Dexterity Test evaluates the ability of a subject to discriminate 2D objects of different sizes/shapes displayed at pre-allocated random locations on the screen or Light panel; or conducting the Visually Guided Dexterity Test with the screen or Light panel displaying light and dark moving stripes/rings of different frequencies and intensities; and evaluating the ability of the subject to detect the direction of motion of the pattern.

It may be that providing the video camera for recording the mobility of the subject may include an infrared LED illumination and may be mounted on a tripod and/or ceiling to record in low-light conditions (approximately than 1 lux), for example.

It may be that the ability of the subject to detect and freely navigate towards the at least one of the Light panel(s) that is emitting light and avoid the obstacles is evaluated by a scoring system, for example. Such a scoring system may have a minimum threshold limit and may be evaluated as a pass or a failure depending on whether the minimum threshold limit is reached for a pass.

It may be that the pre-calibrated Light panel is mounted on an apparatus for controlled illumination. This may provide a consistent and uniform testing for all subjects—a standardized test which provides a consistent light level on every procedure.

The differently shaped Three-dimensional (3D) objects that are stationary or moving may be placed at a stationary or moving base of such an apparatus, for example.

Pressure sensor(s) may be attached to the base of such an apparatus for detecting a change in the pressure when the objects are placed or displaced, for example.

The control board communicating with the computer may also read and communicate with the pressure sensor(s).

The Visually guided Dexterity Test may comprise a Three-dimensional Shape Discrimination which evaluates the ability of a subject (without requiring to be mobile) to detect and discriminate an object and/or motion from a collection of differently sized/shaped/colored stationary/moving objects for near vision evaluation in three-dimensions.

The screen or Light panel may be a touchscreen.

The Visually guided Dexterity Test may comprise a Two-dimensional (2D) Shape Discrimination Test.

The light and dark moving stripes/rings of different frequencies and intensities may move at different speeds and randomized directions.

Evaluating (may involve an Optical Flow Test) the ability of the subject to detect the direction of motion of the pattern may involve a pass or failure (binary).

The subject may have normal vision, or visual impairment in one or both eyes.

The method may comprise the step of evaluating the functional vision of at least one eye of the subject.

It may be that the subject previously received or is expected to receive ocular therapy or surgery in one or both eyes.

The method may comprise the step of assessing the functional vision quantitatively in multiple light intensity levels in subjects with low vision.

It may be that the Light panel(s) or light shining on object(s) provides varying light intensities ranging from 0.1 lux (for example, moonless night) to 100 lux or above (for example, bright outdoor lighting) for evaluation of real-life visually guided mobility and/or dexterity vision in rod driven (at night, for example) and cone driven (during day light, for example) conditions.

The method may comprise the step of assessing the individual S, M or L cone based functional (color) vision by varying the color of light emitted by the Light panel.

The method may comprise the step of comprising evaluating the change in functional vision by scoring the subject's visually guided mobility and dexterity test performance at varying light intensities, with a highest score for passing the test at lowest light intensity and lowest score for not passing the test at highest light intensity.

The method may comprise the step of evaluating functional vision based on success of the completion of a task based on the accuracy of the mobility and dexterity tasks including (i) touching the Light panel while avoiding the obstacles, (ii) touching/picking up the target object, and/or detecting correct direction of motion. This may involve Optical flow.

The method may comprise the step of using multiple Light panels or starting positions, increasing number of obstacles or objects, and/or randomizing the positioning of the objects, obstacles, and subject to minimize a learning effect of the subject while performing the visually guided mobility and dexterity tests.

The method may comprise the step of adjusting the difficulty level of the visually guided mobility and dexterity tests to evaluate subjects with a specific or broad range of ocular diseases based on their functional vision status. The specific diseases may comprise, for example, central, peripheral, or pan-retinal vision loss.

In another aspect, the present invention contemplates an apparatus configured for performing functional vision tests in low vision subjects comprising: a single or multiple Light panel(s) for emitting light or shining light on object(s) at different intensity levels; a single or multiple randomly-selected starting point(s) for a subject to find at least one of the Light panel(s) that is emitting light or the light shining on object(s); a variable number of obstacle(s) positioned at different locations in the path to the Light panel(s) or the light shining on object(s); a video camera for recording the mobility of the subject; a computer for switching at least one of the Light panel(s) ON/OFF, and integrated software operable to vary the light intensity and color of the Light panel(s), wherein the size, shape, and number of Light panels or the light shining on object(s) is selectable;

wherein the Light panel(s) or the light shining on object(s) comprises an LED display operable to generate specific frequency of LED patterns.

Wherein the distance between adjacent Light panel(s) or lighted object(s), and distance between the starting point to the Light panel(s) or the lighted object(s) is selectable;

wherein control of dynamic range of light intensity from the at least one Light panel(s) or the light shining on object(s) is adjustable;

wherein the position of the single or multiple obstacle(s) between the starting point and the at least one Light panel(s) or the light shining on object(s) is adjustable; and a control module for providing instructions to the subject.

Any of the apparatus defined herein may be configured for facilitating any of the methods of evaluating functional vision in low vision subjects as defined herein.

It may be that the video camera for recording the mobility of the subject may include an infrared LED illumination and may be mounted on a tripod and/or ceiling to record in low-light conditions (approximately than 1 lux), for example.

It may be that the panel(s) is adjustable using different types of LED, polarizer and neutral density filter, for example.

It may be that a goggle with different neutral density filters is used by the subject to further attenuate the light intensity reaching the eye.

It may be that the height of Light panel(s) position on the tripod can be adjusted to account for different heights of the subject's eye level.

The position of the single or multiple obstacle(s) between the starting point and the at least one Light panel(s) may be adjustable in different arrangements to adjust the difficulty level of the mobility test;

It may be that the obstacle(s) of different shape, size, and color have different reflectivity, for instance.

The reflectivity from the obstacle(s) may be changed using a polarizing film.

The motion sensors may be mounted on/under the obstacle(s) and/or LED display for automatic detection of obstacle hit by the subject performing the test. Alternatively, the obstacles may be detected/recorded by a human.

A height adjuster may be used to change the height of the obstacle(s) to account for different height of the subjects performing the test.

It may be that the control module for providing instructions to the subject may also direct and record the test and this may be conducted by PC, tablet, or smart devices.

It may be that the accuracy score is calculated based on completion of Light panel(s) touching task, with penalties assigned for each hit of the obstacle(s), and/or time taken to complete the task.

The integrated software may enable directing, making announcement, and/or recording of the performance of test.

In another aspect, the present invention contemplates an apparatus configured for functional vision tests in low vision subjects comprising: a pre-calibrated Light panel for controlled illumination; differently shaped Three-dimensional (3D) objects positioned at the stationary or moving portion of the apparatus; a pressure sensor(s) attached to the apparatus to detect change in the pressure when the objects are placed or displaced; a control board operable to communicate with a computer for controlling the light intensity levels of the Light panel and for reading the pressure sensor(s); integrated software for providing instructions to the subject in randomized order and for recording the performance of test, wherein the distance between adjacent objects, and distance between the mounted Light panel and objects is selectable;

wherein the size, shape of Light panel is selectable;

wherein control of dynamic range of light intensity from the LED panel is adjustable; and a control module for providing instructions to the subject.

It may be that the panel(s) is adjustable using different types of LED, polarizer and neutral density filter, for example.

It may be that the obstacle(s) of different shape, size, and color have different reflectivity, for instance.

The reflectivity from the obstacle(s) may be changed using a polarizing film.

It may be that the 3D shapes objects may be selected but not limited to, Cube, pyramid, sphere.

It may be that the pressure sensors are mounted on/under the object(s) for automatic detection of correct organization of the objects based on different weight as well as identify and record the object picked up by the subject performing the test.

It may be that the control module for providing instructions to the subject may also direct and record the test and this may be conducted by PC, tablet, or smart devices.

It may be that the accuracy score and time score are calculated based on correctness of shape determination, and/or time it takes to complete the task.

The integrated software may enable directing, making announcement, and recording the performance of the test.

In another aspect, the present invention comprehends an apparatus for functional vision tests in low vision subjects comprising multiple types of objects that are displayed at different intensity levels against a background on a screen or Light panel in randomized order, wherein the intensity and color of the objects and background is adjustable;

wherein the objects displayed are stationary or floating within the screen or Light panel(s); and wherein a touch sensor on the screen or Light panel records the screen touch by the subject for analysis.

It may be that a Two-dimensional (2D) Shape Discrimination Test evaluates ability of a subject to discriminate 2D objects of different sizes/shapes displayed at pre-allocated random locations on touchscreen Light panel, wherein the 2D shapes objects may be selected but not limited to, Square, Triangle, and Circle.

The intensity and color of the objects and background may be adjustable to probe different aspects of vision.

In another aspect, the present invention envisages an apparatus for functional vision tests in low vision subjects comprising: multiple types of objects that are displayed at different intensity levels against a background on a screen or Light panel in randomized order, wherein the intensity and color of the objects and background is adjustable;

wherein the objects displayed are stationary or floating within the screen or Light panel; and wherein a touch sensor on the screen or Light panel records the screen touch by the subject for analysis;

The screen or Light panel(s) may be a touchscreen.

It may be that a Two-dimensional (2D) Shape Discrimination Test evaluates ability of a subject to discriminate 2D objects of different sizes/shapes displayed at pre-allocated random locations on touchscreen Light panel(s), wherein the 2D shapes objects may be selected but not limited to, Square, Triangle, and Circle.

The intensity and color of the objects and background may be adjustable to probe different aspects of vision.

In another aspect, the present invention comprehends an apparatus for functional vision tests in low vision subjects comprising: light and dark moving stripes/rings of different frequencies and intensities that are displayed on a screen or Light panel(s) in randomized direction, wherein the intensity and color of the light and dark moving stripes/rings is adjustable;

wherein the speed of the light and dark moving stripes/rings is adjustable; and wherein a touch sensor on the screen or Light panel(s) records the screen touch by the subject for analysis.

The screen or Light panel(s) may be a touchscreen.

In an embodiment, the present invention describes a device and method of Visually Guided Mobility Test evaluating the ability of a subject to detect and freely navigate toward lighted panel at different light intensities avoiding the obstacles. Without any other visual cues for direction such as arrows or markers, this emulates performance of various mobility routines of daily living.

In yet another embodiment, the present invention also provides a device and method to evaluate near vision (near-vision dexterity task) in low-vision subjects (without requiring to be mobile) via discrimination of shape and motion of objects in a two-dimensional (2D) and/or three-dimensional (3D) environment having different light intensities.

In yet another embodiment, the present invention describes a device and method wherein the near vision testing is conducted by displaying 2D Optical Flow (light and dark stripes/rings of different frequencies and intensities moving at different speeds and directions) on a screen wherein the subject is required to detect the direction of motion of the pattern.

In another embodiment, the present invention describes a method of performing the visually guided mobility task and near-vision dexterity task repeatedly at same light intensity level (with randomly arranged shapes and directions of movement) for determining proportion of pass events to determine pass/fail at that light level based on predefined threshold. The pass/fail criteria may include performing the test with score higher than threshold score and test completed within pre-determined cut off time.

According to another embodiment, the present invention describes a device and method of varying the difficulty of the low vision tests by changing the number of light panels, light intensity levels, number of obstacles, and/or reflectivity of the obstacles in mobility test, by changing the light intensity, number, shape, size of the objects in 2D/3D Shape Discrimination tests, by altering the frequency and speed of the displayed stripes in 2D Optical Flow test. Thus, the test can be adapted to evaluate specific as well as broad range of low-vision patients.

In another embodiment, the present invention describes a device and method which is capable of (operable to or configured for) discriminating subjects with different level of vision and capable of monitoring changes in functional vision in low-vision subjects at different time points and/or after therapeutic intervention.

In a broader embodiment, the present invention describes a method of determining change in functional vision by longitudinally scoring the subject's mobility and dexterity performance at varying light intensities. Thus, the present invention describes a device and method (configured) for quantitative measurements of vision level that can be correlated with low-vision subject's real-life visual perception and interaction.

BRIEF DESCRIPTION OF DRAWINGS

The following drawings illustrate by way of example and not limitation. For the sake of brevity and clarity, every feature of a given structure is not always labeled in every figure in which that structure appears. The following drawings form part of the present specification and are included to further demonstrate certain aspects of the present invention. The invention may be better understood by reference to one or more of these drawings in combination with the detailed description of the specification embodiments presented herein.

FIG. 1. is a diagram showing a Visually Guided Mobility Test Setup. 1001: LED panel 1; 1002: LED panel 2; 1003: Center obstacle(s); 1004: Left obstacle(s); 1005: Right obstacle(s); 1006: Subject start position; 1007; PC and monitor/laptop/tablet; 1008: Video camera;

FIG. 2A. is a diagram showing a Visually Guided Mobility Test component—LED panel. Different size and shapes of LED panel are used, and the LEDs emit different colors. Also, different elements or arrays of LED within the LED panel were lighted to generate LED stripes and patterns. For further control of dynamic range of light intensity from LED, a polarizer (1001) and/or neutral density filter (1002) is used;

FIG. 2B. is a diagram showing a Visually Guided Mobility Test component—Obstacle(s). Different color, reflectivity, size and shapes of obstacle(s). Polarizing film (1001) is utilized to further change the reflectivity of obstacle(s);

FIG. 2C. is a diagram showing a Visually Guided Mobility Test component—Control Module. PC, or tablet for synchronization and control of the test;

FIG. 3A. is a diagram showing a Configuration 2 of Visually Guided Mobility Test Setup. 1001: LED panel 1; 1002: LED panel 2; 1003: LED panel 3; 1004: Left obstacle(s); 1005: Center obstacle(s); 1006: Right obstacle(s); 1007: Subject start position; 1008: Video camera; 1009: PC and monitor/laptop/tablet;

FIG. 3B. is a diagram showing a Configuration 3 of Visually Guided Mobility Test Setup. 1001: LED panel 1; 1002: LED panel 2; 1003: Left obstacle; 1004: Right obstacle; 1005: Left obstacle(s); 1006: Center obstacle(s); 1007: Right obstacle(s); 1008: Subject start position; 1009: Video camera; 1010: PC and monitor/laptop/tablet;

FIG. 3C. is of a picture showing the arrangement of obstacles and 3 light panels as seen in FIG. 3A;

FIG. 4C. is a scattered light map of the obstacles at the starting position under different luminance levels. 0.3 Lux measured at starting position at eye level—when the visibility data is collected with the left LED panel was ON;

FIG. 4D. is a scattered light map of the obstacles at the starting position under different luminance levels. 1 Lux measured at starting position at eye level—when the visibility data is collected with the left LED panel was ON;

FIG. 4E. is a scattered light map of the obstacles at the starting position under different luminance levels. 3 Lux measured at starting position at eye level—when the visibility data is collected with the left LED panel was ON;

FIG. 4F. is a scattered light map of the obstacles at the starting position under different luminance levels. 10 Lux measured at starting position at eye level—when the visibility data is collected with the left LED panel was ON;

FIG. 4G. is a scattered light map of the obstacles at the starting position under different luminance levels. 32 Lux measured at starting position at eye level—when the visibility data is collected with the left LED panel was ON;

FIG. 4H. is a scattered light map of the obstacles at the starting position under different luminance levels. 100 Lux measured at starting position at eye level—when the visibility data is collected with the left LED panel was ON;

FIG. 4M. is an image of the Luminance distribution in the Visually Guided Mobility Test as measured by light meter. Map of luminance in room from the light source and scattered light from the obstacles as seen by the subject. The non-uniformity of the illumination path (created by obstacles and their reflection) for the light level of 32 Lux. Scale bar: Lux;

FIG. 4N. is an image of the Luminance distribution in the Visually Guided Mobility Test as measured by light meter. Map of luminance in room from the light source and scattered light from the obstacles as seen by the subject. The non-uniformity of the illumination path (created by obstacles and their reflection) for the light level of 100 Lux. Scale bar: Lux;

FIG. 5. is an image of a Graphical User Interface for Visually Guided Mobility Test. Testing Eye Tab: Input which eye (OS/OD/OU) to be tested; Light Control Tab: Turn on/off specific LED panel (left or right) or random LED panels for testing; Intensity Control Tab: Input light intensity level for LED panel; Test Control Tab: Start and end test (inbuilt timer to track the time elapse synchronized with video camera recording; Obstacle Tab: Record which obstacles were hit during the test; Save tab: Save the test parameters and result;

FIG. 6. Is a Flowchart of Visually Guided Mobility Test. 1001: Test instruction provided to subject; 1002: Light level intensity selection; 1003 Start the Visually Guided Mobility Test; 1004: Synchronized video record and timer start; 1005: Single randomized LED panel light up; 1006: Record any obstacle(s) hit in software during test, and test ends if the subject finds the lighted LED panel or timer runs out; 1007: Repeat the test for N number of times at the same light intensity level; 1008: Light level increase; 1009: Repeat the test protocols for M number of intensities;

FIG. 7A. is an image of a Scoring system of Visually Guided Mobility Test. 1001: Assign penalty weights for obstacle-hit(s), repositioning, cut-off test time, pass/fail threshold score. 1002; Compute the final score (Accuracy score) from data collected within a trial and assigned weights; 1003: Compare with pass/fail threshold score to determine pass or fail for the trial; 1004: Determine if the subject passes the light level by comparing to the proportion of trial pass criteria set for overall passing of a light level; 1005: Determine lowest level of illumination subject passes;

FIG. 7B. is an image of an Example of a scoring system for visually guided mobility test. Penalty weights of any obstacles hit, going out of boundary such as hitting the wall of the room, and repositioning are assigned differently. If subject touches the correct LED light panel, the subject earns certain points (ex, 100). Pass/fail threshold value is set to be threshold for pass criteria for each trial. The subject is considered pass if final calculated score (Accuracy score) is higher than pass threshold value;

FIG. 9A. is a Plot of accuracy score vs. time score in low vision subjects. The straight lines represent fit for determining correlation between accuracy and time scores;

FIG. 9B. is a Plot of accuracy score vs. time score in better vision subjects;

FIG. 9C is a chart showing Variation of the Visually Guided Mobility Test score with BCVA and discriminant validity. N=8;

FIG. 12A. is a picture of a 3D shape discrimination framework and procedure example. Three different types of object places on the base of 3D Shape Discrimination apparatus mounted with pressure sensor. The flat LED panel from the top of the device controls light intensity level;

FIG. 12B is a picture of an Example of a subject picking up an instructed object in the 3D shape discrimination test;

FIG. 12C. is an image of an Example of output from the 3D Shape Discrimination assay. Light intensity, object portion information, target shape and location, shape of object picked up by a subject, and correctness of the 3D Shape Discrimination are provided;

FIG. 13A. is a diagram of a 2D shape discrimination: Three different types of are displayed in touchscreen in a random arrangement order;

FIG. 13B. is diagram of Another display option with floating objects in randomized manner. Which object to be picked up is announced (by proctor according to the GUI, or by automated voice in the software). The test ends when the subject touches the touchscreen regardless of correctness;

FIG. 13C. is a chart of a Correlation of 2D size threshold score with BCVA (measured by Freiburg Acuity) into different groups of low vision patents;

FIG. 13D. is a plot of a Correlation of 2D shape Discrimination accuracy with BCVA;

FIG. 13E. is an Example of output from the 2D Shape Discrimination assay. Light intensity, shape position information, target shape and location in XY coordinates, shape of object selected by a subject, XY coordinates of the touch input, elapsed time and correctness of the shape discrimination are recorded;

FIG. 14A. is an Optic flow moving towards the left;

FIG. 14B. is an Optic flow moving towards up (in an upwardly direction) in the 2D optical flow discrimination test. Black and white stripes at different frequency that flow into random directions are displayed in touchscreen. The subject is asked to tell which direction the flow is moving or asked to touch the side of touchscreen where the flow is moving towards;

FIG. 14C. is an image showing an Example of output from the 2D optical flow determination assay. Flow direction, XY coordinates of the touch input, elapsed time and correctness of the flow direction determinations are provided;

DETAILED DESCRIPTION OF THE INVENTION

Figure 3D:
FIG. 3D. is an image of a low-vision subject performing the test, navigating through the obstacle course shown in FIG. 3C, ending with touching the (randomly)-lit panel.

Severe to near-total loss of vision in patients occurs due to variety of ocular diseases including inherited retinal degenerations, age related macular degeneration, retinal detachment, optic nerve abnormality, cataract, glaucoma and corneal abnormality. Types of loss of vision is varied from central to peripheral loss, reduced contrast sensitivity and night blindness. Though there exists number of devices such as FST, ERG, HVF to measure visual function in low-vision subjects, individually, these methods provide measure of single-parameter (e.g. intensity threshold in FST). Further, it is unclear if these existing tests measure a clinically meaningful outcome, and are, therefore, not widely accepted as a primary efficacy endpoint for low-vision studies. Therefore, there is a need for development of a validated multi-parameter test for static and moving object recognition.

Early Treatment Diabetic Retinopathy Study (ETDRS)[5] visual acuity chart has been accepted as an endpoint supporting approval in many retina studies, but cannot be used for very low vision (BCVA worse than 20/800) patients. A standard ETDRS visual acuity chart is designed for visual acuities of 20/800 (logMAR 1.0) to 20/10 (Snellen visual acuity equivalent). Traditional vision testing charts are not able to measure vision below a certain level. Vision in this range is classified as counting fingers (CF), hand movements (HM) and light perception (LP). These measures are not very accurate or easily quantifiable. They are also poorly understood in terms of impact on quality of life. Freiburg Visual Acuity Test (FrACT)[6] is a computer-based test developed to assess patients down to the LP level. However, bedsides VA assessments, measurement of functional vision is key to assess the ability of low-vision patients to perform activities of daily living.

With the increase in regenerative medicine, especially gene and cell therapy, targeting different cell types to halt degeneration, refunctionalize cells or integrate new cells, assessment of different and novel parameters for very low vision subjects is becoming increasingly important. Without being able to accurately measure the change in functional vision before and after treatment, it is not possible to fully assess the effect of treatment.

Multi-Luminance Mobility Test (MLMT)[7] has been used to measure functional vision in low vision patients, but cannot be used for very low vision (BCVA worse than 20/200) patients. Further, evaluating mobility performance within a set time may not be feasible for low-vision patients with difficulty in mobility.

To meet the challenges, the present invention provides a device and method for assessing functional vision in low vision patients, mimicking daily activities at varying light intensities such as walking towards a lighted window or doorway, avoiding obstacles, as well as picking up objects on a table.

In an embodiment, the present invention describes a device and method of evaluating the ability of a subject to detect and freely navigate towards a lighted panel at different light intensities avoiding the obstacles, without any other visual cues for direction such as arrows or markers. Thus, this emulates performance of various mobility routines of daily living.

In an embodiment, the present invention describes a device and method of evaluating the navigation performance wherein the functional vision of each eye as well as both eyes are evaluated based on the subject's ability to find a randomly-selected lighted panel that provides varying light intensities ranging from moonless night (<0.5 lux) to bright outdoor lighting (≥100 lux), measured at the starting point at the eye level of the subject. The discrete light intensities can be standardized (via calibrated lux meter) to have a semi-log difference and may include one or more of 0.3 lux, 1 lux, 3 lux, 10 lux, 32 lux, 100 lux, and/or other intensity levels. Thus, the present invention allows evaluation of real-life navigational vision in night (rod driven) and day light (cone driven) conditions.

In another embodiment, the present invention describes a device and method of increasing the dynamic range of the light intensities by use of LED panels with different sizes and colors, control of the LED current, use of polarizers and neutral density filters in the mobility assessment module. Therefore, in addition to evaluating overall cone functions, individual S, M or L cone-based functional (color) vision can be assessed.

According to another embodiment, the present invention describes a device and method of varying the difficulty of the mobility test by changing the number of light panels, light intensity levels, number of obstacles, and/or reflectivity of the obstacles. Thus, the test can be adapted to evaluate specific as well as a broad range of low-vision patients.

In another embodiment, the present invention describes a device and method of performing the navigation test wherein minimization of learning effect is ensured by randomly selecting the lighted panel and/or having multiple start-position (with randomized selection) for the test. Further, height of the LED panels and obstacles are adjusted considering the difference in heights of different subjects.

In an embodiment, the present invention describes a device and method of assigning penalties for hitting obstacles and determining overall score upon completion of the assigned mobility task (finding lighted panel) within cutoff time. Obstacle hitting event(s) are determined based on direct observation, or motion sensor(s) and/or review of recorded video by trained analyst(s). Additional penalties may be assigned for repositioning a subject in case the subject goes out of the test boundaries or safety reasons.

In another embodiment, the present invention describes a method of performing the navigation test repeatedly at the same light intensity level (with randomly selected lighted panel or start position) for determining proportion of pass events to determine pass/fail at that light level based on a predefined threshold. The pass/fail criteria may include performing the test with a score higher than the threshold score and test completed within a pre-determined cut off time.

In yet another embodiment, the present invention also provides a device and method to evaluate near vision (objects within hand reach distance) in low-vision subjects (without requiring to be mobile) via discrimination of shape and motion of objects in a two-dimensional (2D) and/or three-dimensional (3D) environment having different light intensities.

In a further embodiment, the present invention describes a near-vision evaluation device and method based on the ability of a subject (without requiring to be mobile) to detect and discriminate an object from a collection of differently shaped objects at different light intensities ranging from moonless night (<0.5 lux) to bright outdoor lighting (≥100 lux), measured at the patient eye level. The discrete light intensities can be standardized (via calibrated lux meter) to have a semi-log difference and may include one or more of 0.3 lux, 1 lux, 3 lux, 10 lux, 32 lux, and/or other luminance levels. Thus, this emulates performance of various dexterity routines of daily living. Thus, the present invention allows evaluation of real-life near vision in night (rod driven) and day light (cone driven) conditions.

In another embodiment, the present invention describes a near-vision evaluation device and method based on the ability of a subject (without requiring to be mobile) to detect and discriminate an object and/or motion from a collection of differently shaped stationary/moving objects using one eye or both eyes, wherein the color and reflectivity or contrast of the objects along with the color and intensity of the illuminating light may also be altered. Therefore, in addition to evaluating overall cone functions, individual S, M or L cone-based functional (color) near vision can be assessed.

In an embodiment, the present invention describes a device and method enabling testing of the ability of a subject to discriminate 3D objects of different sizes/shapes, optionally on pressure sensors, placed randomly at pre-allocated locations under a controlled lighting environment. The subject is asked by proctor or the device to pick up a target-shaped object at a pre-defined location and under preset lighting parameters (color, intensity). Time cutoff may be provided to complete the task and either the pressure-sensor and/or the proctor records the target-object and object picked up the subject. The functional vision assessments can provide changes in accuracy (%) of the 3D shape detection that can be correlated to changes in near vision.

In another embodiment, the present invention describes a device and method enabling testing of the ability of a subject to discriminate 2D objects of different sizes/shapes displayed at pre-allocated random locations on touchscreen, wherein the intensity and color of the objects and background is controlled. This test emulates the ability of a subject to be able to use smart display devices (used in daily activities such as cell phones, tablets, computers). The subject is asked by proctor or the device to select (by finger touch) a target-shaped object at a pre-defined location on the screen and under preset lighting parameters (color, contrast). Time cutoff may be provided to complete the task and either the screen-sensor and/or the proctor records the target-object and object selected by the subject. The device touch screen interface obtains touch coordinates with respect to the center of the target-object to determine positioning accuracy and provides scatter plot of all trial outcomes.

In yet another embodiment, the present invention describes a device and method wherein the near vision testing includes evaluation of the ability of a subject to discriminate different shaped objects that are in constant motion in a random or defined manner.

In yet another embodiment, the present invention describes a device and method wherein the near vision testing includes evaluation of size threshold for correctly detecting different shapes. The device and method involve size of displayed objects varied from 1-30 degrees (at subject's eye). Ability of the subject to accurately detect smaller size objects imply better vision.

In yet another embodiment, the present invention describes a device and method wherein the near vision testing is conducted by displaying 2D Optical Flow (light and dark stripes/rings of different frequencies and intensities moving at different speeds and directions) on a screen wherein the subject is required to detect the direction of motion of the pattern. The discrete light intensities can be standardized (via calibrated lux meter) to have a semi-log difference and may include one or more of 0.3 lux, 1 lux, 3 lux, 10 lux, 32 lux, and/or other luminance levels. The range of speed varies from 1 deg/sec to 300 deg/sec, or any value in between or fractions thereof. The directions of movement include left-right, up-down, or radially inward/outward. The subject provides input via touch screen or verbally to the proctor regarding his/her perceived direction of movement. In addition, the in-build camera of the display device may track the eye movement during the test. The test measures accuracy (%) of determining direction of Optical Flow as well as the upper speed threshold.

In another embodiment, the present invention describes a device and method which is capable of discriminating subjects with different levels of near-vision and capable of monitoring changes in functional vision in low-vision subjects at different time points and/or after therapeutic intervention.

In another embodiment, the present invention describes a method of performing the near-vision dexterity task repeatedly at same light intensity level (with randomly arranged shapes and directions of movement) for determining proportion of pass events to determine pass/fail at that light level based on predefined threshold. The pass/fail criteria may include performing the test with score higher than threshold score and test completed within pre-determined cut off time.

In a broader embodiment, the present invention describes a method of determining change in functional vision by longitudinally scoring the subject's mobility and dexterity performance at varying light intensities. Thus, the present invention describes a device and method for quantitative measurements of vision level that can be correlated with low-vision subject's real-life visual perception and interaction.

The present disclosure will now be described more fully hereinafter with reference to the accompanying drawings, in which some exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternative are mutually exclusive, although the disclosure supports a definition that refers to only alternatives and "and/or."

The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

Throughout this application, the term "about" is used to indicate that a value includes the standard deviation of error for the device or method being employed to determine the value.

Further, a device or method that is configured in a certain way is configured in at least that way, but it can also be configured in other ways than those specifically described.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Any embodiment of any of the apparatuses, devices, systems, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

To the extent that any specific disclosure in the aforementioned references or other literature may be considered to anticipate any generic aspect of the present invention, the disclosure of the present invention should be understood to include a proviso or provisos that exclude of disclaim any such species that were previously disclosed. The aspects of the present invention, which are not anticipated by the disclosure of such literature, are also nonobvious from the disclosure of these publications, due at least in part to the unexpectedly superior results disclosed or alleged herein.

Below, the presently disclosed invention will be further described by way of examples, which are provided for illustrative purposes only and accordingly are not to be construed as limiting the scope of the invention.

EXAMPLES

We have developed a device and method for determining functional vision in subjects with low vision.

Example 1: the Visually Guided Mobility Test measures changes in functional vision, as assessed by the ability of a subject to navigate accurately and at a reasonable pace at different levels of illumination. Example of visually guided mobility test set up is shown in FIG. 1. In the visually guided mobility test, the subject (1006) is asked to walk towards a Light Emitting Diode (LED) panel (1001 or 1002) lighted at different levels of illumination while avoiding obstacles (1003, 1004, 1005). Videos of subjects undergoing visually guided mobility test are recorded using a camera(s) (1008) that is/are mounted on a tripod for front view and/or in the ceiling for top-view. The height of the camera position on the tripod is adjustable to account for different heights of the subjects performing the test. The camera is equipped with infrared LEDs to enable imaging in a low luminance (or dark) environment. The synchronized video recording, switching ON/OFF of the LED panels, and LED panel light intensity are controlled by a PC (1007) (a control module).

Example 2: Each component of the Visually Guided Mobility Test is chosen to have different properties. As shown in FIG. 2A, different size and shapes of LED panel are used, and the LEDs emit different colors (red, green, blue and white) that allow the assessment of color specific functional vision. Also, different elements or arrays of LED within the LED panel are lighted to generate specific spatial frequency of LED stripes and patterns. For further control of dynamic range of light intensity from LED panel (FIG. 2A) a polarizer (1001) and/or neutral density filter (1002) is used to attenuate the light. The height of the LED panel position on the tripod can be adjusted to account for different heights of the subjects performing test. FIG. 2B shows that the obstacles(s) of different shape, size, and color having different reflectivity. The reflectivity from the obstacles (FIG. 2B) could be changed by use of a polarizing film (1001), for instance. The obstacles are mounted on motion sensors (1002) for automatic detection of the obstacle-hit by the subjects performing the test. A height adjuster (1003) allowed changing the height of the obstacles to account for different height of the subjects performing test. Finally, the control module is selected from a PC or portable tablet for synchronization and control of the LED lights (intensity, ON/OFF, color), and camera recording as shown in FIG. 2C.

Figure 3E:
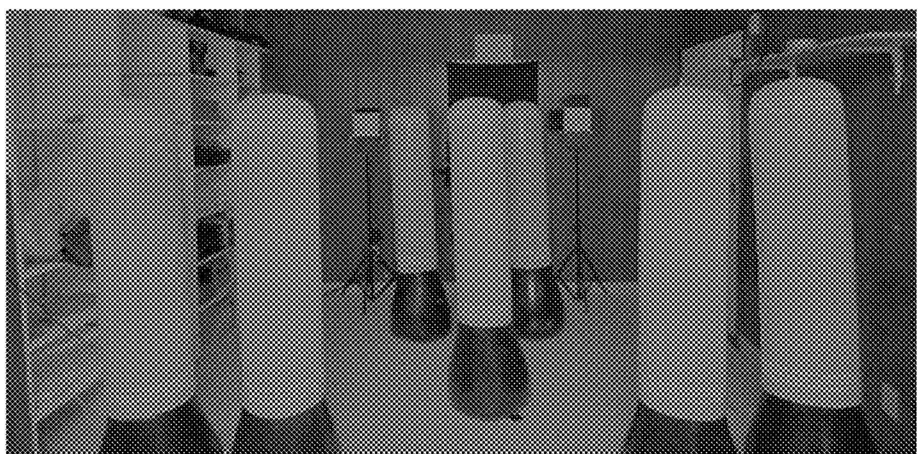
FIG. 3E. is a picture showing the arrangement of obstacles and 2 light panels as seen in FIG. 3B.
Figure 3F:
FIG. 3F. is a picture of a low-vision subject (CF 1') performing the test, navigating through obstacle course shown in FIG. 3E, and ending with touching the (randomly)-lit panel.
Figure 3G:
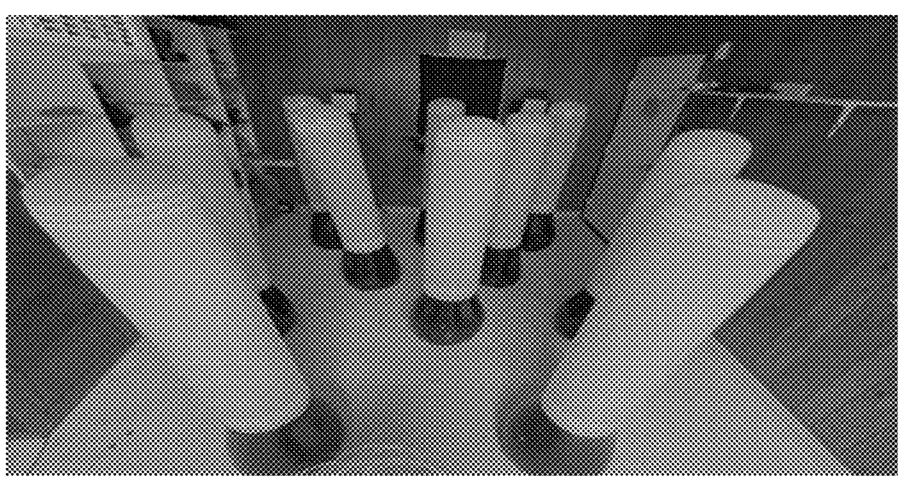
FIG. 3G. is a picture showing a variation in the arrangement of obstacles shown in Visually Guided Mobility Test with 2 light panels.
Figure 3H:
FIG. 3H. is a picture of a low-vision subject performing the test, navigating through the obstacle course shown in FIG. 3G, and ending with touching the (randomly)-lit panel.

Example 3: Multiple possible configurations of Visually Guided Mobility Test are shown in FIG. 3A and FIG. 3B. Additional number of LED panels (1001, 1002, 1003) are placed as shown in FIG. 3A. Further, different arrangements and number of obstacle(s), to adjust difficulty level of the mobility test, are placed as demonstrated in FIG. 3B. The visually guided mobility set up design is adapted to the vision-status, and mobility of the subject population. Practical setup based on three LED setup from FIG. 3A is visible in FIG. 3C. Low vision subject shown navigating obstacle setup to touch the randomly turned-on LED panel in FIG. 3D. The complexity of the Visually Guided Mobility Test setup was increased by additional obstacles and positioning of the obstacles near the light sources were increased as shown in FIG. 3E. Low vision subject shown navigating towards randomly lit LED panel while avoiding obstacles in FIG. 3F. Alteration of obstacle pattern and light panel positioning leads to a multitude of increased difficulty in navigation for visually impaired subjects. The complexity of the Visually Guided Mobility Test set-up was increased by additional obstacles and positioning of the obstacles in a checkerboard pattern as shown in FIG. 3G. Subject shown navigating checkboard pattern maze to find randomly lit LED panel in FIG. 3H. Increasing the number of LED panels or altering the number of paths eliminates the easy decision of left or right when no clear path forward is presented.

Figure 4A:
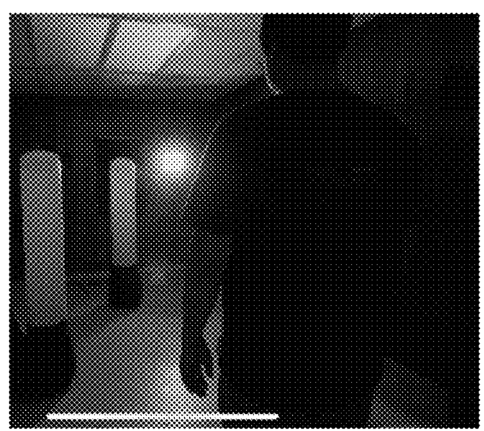
FIG. 4A. is of an image of a Visually Guided Mobility Test procedures: Beginning of the test; Subject positioned at the start line, and randomly lighted LED panel.
Figure 4B:
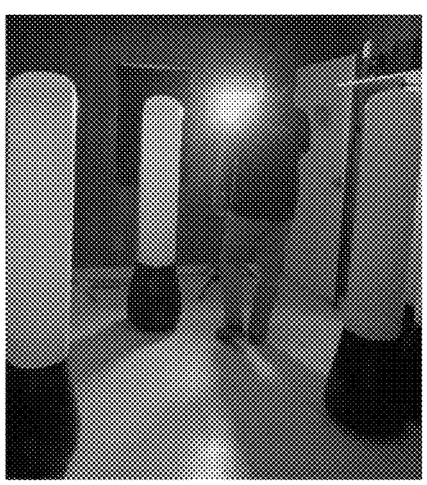
FIG. 4B. is an image taken at the End of the test; Subject finding/touching lighted LED panel after navigating through obstacles.
Figure 4C:
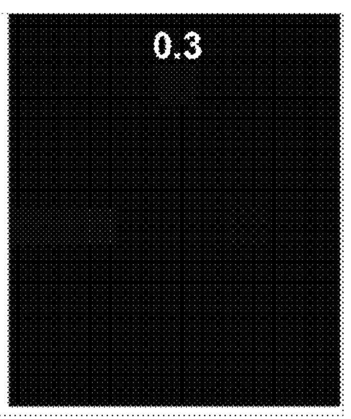
Figure 4D:
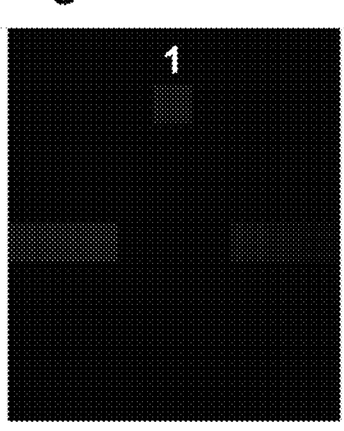
Figure 4E:
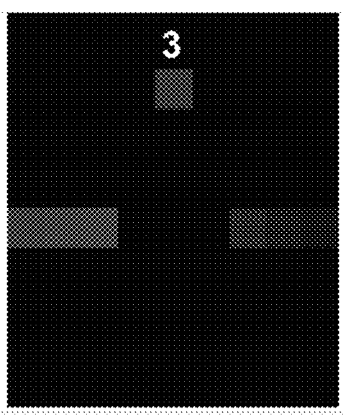
Figure 4F:
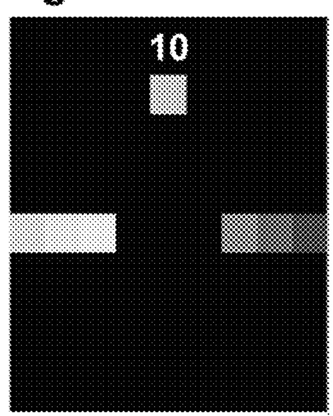
Figure 4G:
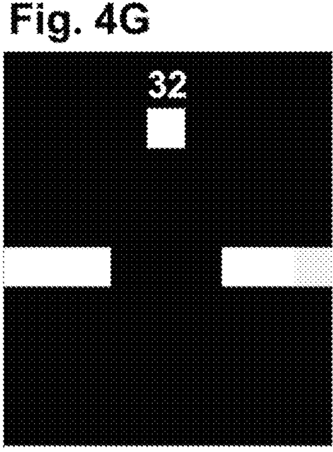
Figure 4H:
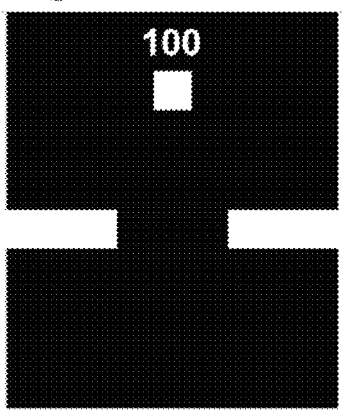
Figures 4I, 4J, 4K, 4L:
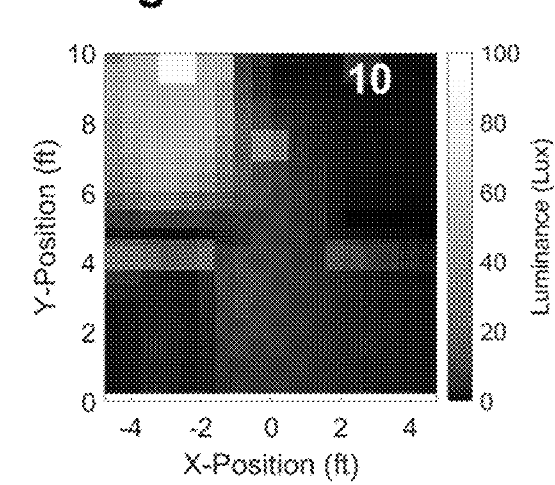
FIG. 4I. is an image of the Luminance distribution in the Visually Guided Mobility Test as measured by light meter. Map of luminance in room from the light source and scattered light from the obstacles as seen by the subject. The non-uniformity of the illumination path (created by obstacles and their reflection) for the light level of 0.3 Lux. Scale bar: Lux.
FIG. 4J. is an image of the Luminance distribution in the Visually Guided Mobility Test as measured by light meter. Map of luminance in room from the light source and scattered light from the obstacles as seen by the subject. The non-uniformity of the illumination path (created by obstacles and their reflection) for the light level of 1 Lux. Scale bar: Lux.
FIG. 4K. is an image of the Luminance distribution in the Visually Guided Mobility Test as measured by light meter. Map of luminance in room from the light source and scattered light from the obstacles as seen by the subject. The non-uniformity of the illumination path (created by obstacles and their reflection) for the light level of 3 Lux. Scale bar: Lux.
FIG. 4L. is an image of the Luminance distribution in the Visually Guided Mobility Test as measured by light meter. Map of luminance in room from the light source and scattered light from the obstacles as seen by the subject. The non-uniformity of the illumination path (created by obstacles and their reflection) for the light level of 10 Lux. Scale bar: Lux.

Example 4: FIG. 4A and FIG. 4B illustrate examples of visually guided mobility test performance. The subject is positioned at the starting position and a random LED panel is turned on to produce desired light intensity level as shown in FIG. 4A. The subject navigates around the obstacles and the test ends when the subject touches the lighted LED panel as shown in FIG. 4B. The proctor/motion sensors recorded the obstacles that are hit during the test. The video is also recorded for verification. In this example, translucent obstacles are positioned left, right and center of the test with two LED panels at the end (as in FIG. 1) while maintaining controlled low luminance level environment for the testing (<1 lux ambient room light). FIG. 4C illustrates a visual top-down representation of objects based on the configuration shown in FIG. 1. Each obstacle reflects light corresponding to the activated LED panel during the test. At the lowest luminance level (0.3 lux), the visibility of the obstacles remains poor, and the visibility increases as the LED intensity is increased. As expected, the left side obstacles visibility is higher when the left LED panel is ON compared to right obstacles, and the same is true when the right LED panel is ON. Although the assumption is that the left LED panel is active for the top-down representation, the graphic can be vertically mirrored to depict the scenario when the right LED panel is active. FIG. 4D shows a slightly more defined layout at 1 Lux. FIG. 4E shows a fully defined left and middle obstacle with the right side being lowly lit at 3 Lux. FIG. 4F shows a brightly lit middle and left side with the right side being clearly defined at 10 Lux. FIG. 4G shows the fully illuminated left and middle obstacles at 32 Lux. FIG. 4H shows the fully illuminated obstacles at 100 Lux. A total of 9×10 measurements per luminance level were made excluding the top row where the light panel is located. The light intensity map, and the obstacle scattering map, were overlaid to represent what a subject would see at a given position navigating through the Visually Guided Mobility Test shown in FIG. 4I. The luminance map across different areas within the room for the Visually Guided Mobility Test, as measured from the subject's perspective using a light meter, for different luminance levels 0.3 FIG. 4I, 1 Lux for FIG. 4J, 3 Lux for FIG. 4K, 10 Lux for FIG. 4L, 32 Lux for FIG. 4M, and lastly 100 Lux for FIG. 4N all measured from the starting position.

Example 5: FIG. 5 shows the Graphical User Interface for Visually Guided Mobility Test. In the "Testing Eye" tab, the proctor provided inputs which eye-open condition for the subject (Monocular: OS, OD or Binocular: OU) is to be tested. In the "Light Control" tab, the proctor manually checked if the LED panels are functioning or not. According to the test protocol, desired light intensity and light color are selected in the "Intensity Control" and "Color control" tabs respectively. The upper tabs are designed to include the controllable parameters of individual test trial by a proctor. Once the subject is positioned at the starting line, the proctor starts the test in the Test Control tab. Once the Start button is pressed, the timer starts as well as recording of the video as shown in the bottom right tab. During the test, the proctor inputs which obstacle are hit by the subject in the Obstacle tab. The timer ends when End button in the Test Control tab is pressed, and the proctor records the input parameters and results in Save tab.

Example 6: FIG. 6 illustrates a sequence (flow chart) of the procedure in a Visually Guided Mobility Test. First, the test instruction is provided to the subject (1001), and lowest light intensity is selected (1002). When the test starts (1003), the synchronized video and timer starts (1004) and the randomly selected LED panel is lighted (1005). The subject navigates around the obstacles to touch the lighted LED panel, while the proctor records in the software any obstacle(s) hit during the test. The motion sensor(s) associated with the obstacle(s) also records obstacle(s) hit in software independently and/or alternatively. The test ends when the subject finds the lighted (correct) LED panel or pre-set timer runs out (1006). After completing a trial, repeated tests are performed at the same light intensity level where new randomized LED panel is lighted up on each trial (1007). After completing the predetermined number of trials for each light level, the proctor changes the light intensity level (1008) and repeats the test protocols until reaching the maximum light intensity level.

Example 7: This example shows how the visually guided mobility test is implemented to assess and discriminate subjects with different levels of functional vision by adjusting the levels of difficulty in performing/passing the test. This includes adjustment of the range (lowest and highest) of light intensity levels and location of different obstacles within the test as described in Example 3. In addition to physical adjustments of the components and configuration of the test, various scoring systems are assigned to adjust sensitivity as well as dynamic range of the assay considering different functional vision level. FIG. 7A demonstrates a scoring system of Visually Guided Mobility Test. First, individual penalty weights for obstacle-hit(s), repositioning (required when subject is completely off-the mobility course), cut-off test time as well as pass/fail threshold score are assigned (1001). Repositioning of subject (within pre-determined cut off time) is conducted when there is a safety issue and/or when the subject is completely lost of visually-guided task and touches the non-lighted (wrong) panel. Once penalty weights are assigned, final score is computed from data collected within each trial (1002). The computed score of each trial is compared to the pass/fail threshold score (1003). Depending on the proportion of trial pass criteria set for overall passing of a light level, the subject's trial-performance is evaluated for pass/fail of the specific light level (1004). When all calculations are finished for all tested light intensity levels, the lowest light illumination level (1005) that subject passed (light intensity level in which the proportion of trial pass criteria is met) is determined.

FIG. 7B shows example of scoring system for the Visually Guided Mobility Test (FIG. 1). The penalty weights of any obstacle(s) hit, going out of boundary such as hitting the boundary of the test area (such as wall of the room), and repositioning are assigned differently. In this example, left and right obstacle(s) have a weight C1, center obstacle(s)

have a weight C3, out of boundary have a weight C4, and repositioning have a weight C5. N1 through N5 represent number of hits with corresponding obstacle(s) and number of other penalties during the test. The subject earns Screen Touch Score (e.g., 100 points) if he/she touches the lighted LED panel, and the final score is calculated by an equation, Accuracy Score=Screen Touch Score−C1*N1−C2*N2−C3*N3−C4*N4−C5*N5. If the trial score is higher than X, which is pass/fail threshold value, the subject is considered passing that specific trial.

Figure 8A:
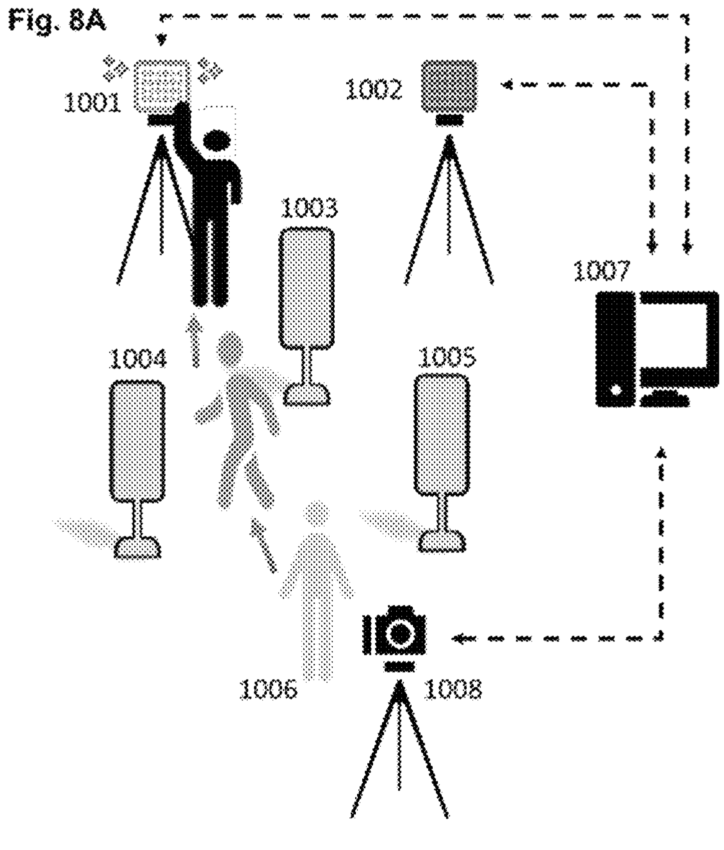
FIG. 8A. is a diagram showing a Visually Guided Mobility Test Scenario 1. 1001: LED panel 1 (on); 1002: LED panel 2 (off); 1003: Center obstacle(s); 1004: Left obstacle(s); 1005: Right obstacle(s); 1006: Subject start position; 1007; PC and monitor/laptop/tablet; 1008: Video camera. The subject navigates and touches the lighted LED panel without bumping any obstacles. Number of Left/Right obstacle(s) hit=0; Number of Center obstacle(s) hit=0; Number of Out of boundary=0; Number of Repositioning=0; Touched lighted panel=Yes.
Figure 8B:
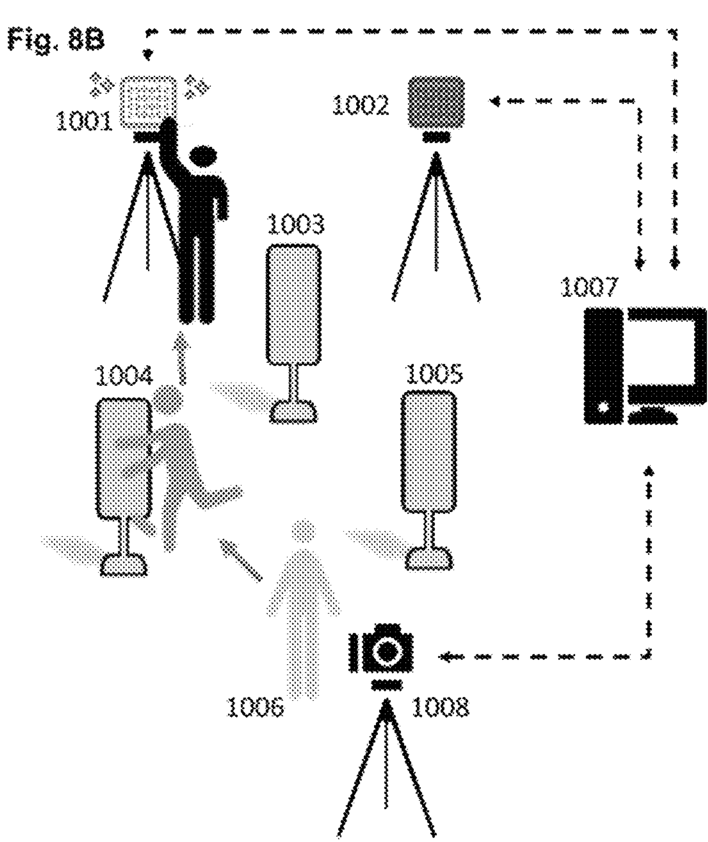
FIG. 8B. is a diagram showing a Visually Guided Mobility Test Scenario 2. 1001: LED panel 1 (on); 1002: LED panel 2 (off); 1003: Center obstacle(s); 1004: Left obstacle(s); 1005: Right obstacle(s); 1006: Subject start position; 1007; PC and monitor/laptop/tablet; 1008: Video camera. The subject bumps left obstacle(s) once, then navigates to touch the lighted LED panel without bumping any additional obstacle(s). Number of Left/Right obstacle(s) hit=1; Number of Center obstacle(s) hit=0; Number of Out of boundary=0; Number of Repositioning=0; Touched lighted panel=Yes.
Figure 8C:
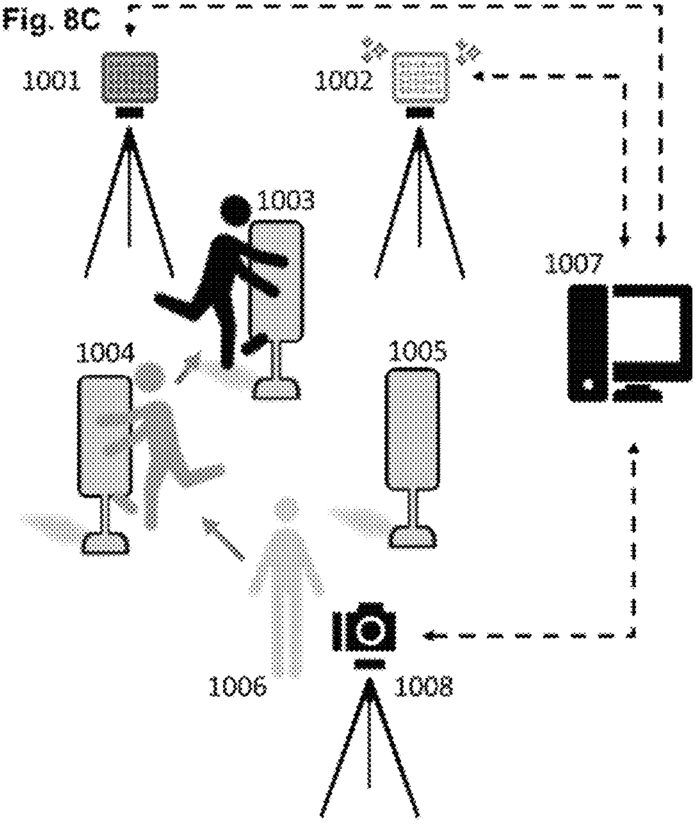
FIG. 8C. is a diagram showing a Visually Guided Mobility Test Scenario 3. 1001: LED panel 1 (off); 1002: LED panel 2 (on); 1003: Center obstacle(s); 1004: Left obstacle(s); 1005: Right obstacle(s); 1006: Subject start position; 1007; PC and monitor/laptop/tablet; 1008: Video camera. The subject bumps left obstacle(s) once, then bumps into the center obstacles(s) once and never find/touch the lighted LED panel. Number of Left/Right obstacle(s) hit=1; Number of Center obstacle(s) hit=1; Number of Out of boundary=0; Number of Repositioning=0; Touched lighted panel=No.

Example 8: FIG. 8A, FIG. 8B, and FIG. 8C depict several scenarios of scoring by the subject in the Visually Guided Mobility Test. In example FIG. 8A, the left LED panel is lighted (lit), and the subject navigates and touches the lighted LED panel without bumping any obstacles. Number of Left/Right obstacle(s) hit=0; Number of Center obstacle(s) hit=0; Number of Out of boundary=0; Number of Repositioning=0; Touched lighted panel=Yes. Using the scoring system described earlier, the accuracy score is calculated as Score=100 (Screen Touch)−C1*0−C2*0−C3*0−C4*0−C5*0=100. In example FIG. 8B, the left LED panel is lighted, and the subject bumps left obstacle(s) once, then navigates to touch the lighted LED panel without bumping any additional obstacle(s). Number of Left/Right obstacle(s) hit=1; Number of Center obstacle(s) hit=0; Number of Out of boundary=0; Number of Repositioning=0; Touched lighted panel=Yes. Similarly, the accuracy score is calculated as Score=100 (Screen Touch)−C1*1−C2*0−C3*0−C4*0−C5*0=100−C1.

In the example of FIG. 8C, the right LED panel is lighted; however, the subject bumps left obstacle(s) once, then bumps into the center obstacles(s) once and never find/touch the lighted LED panel. Number of Left/Right obstacle(s) hit=1; Number of Center obstacle(s) hit=1; Number of Out of boundary=0; Number of Repositioning=0; Touched lighted panel=No. In this case, the accuracy score is calculated to be Score=0 (No Screen Touch)−C1*1−C2*1−C3*0−C4*0−C5*0=−C1−C2. In these examples, left and right obstacle(s) weights are assigned the same, but different weights are assigned for left and right obstacle(s) depending on which LED panel is lighted for other mobility test configurations. If value of C1 is 20, value of C2 is 30, and pass accuracy score threshold is higher than 50 points, the subject in FIG. 8A passes the trial with an accuracy score of 100, the subject in FIG. 8B passes the test with a score of 80, but the subject in FIG. 8C fails the trial with accuracy score of −50.

Example 9: Visually Guided Mobility Test has been validated with subjects with different visual impairments. FIG. 9A shows plot of accuracy score vs. time score in low vision subjects. In this example, to pass the test, the subject has to achieve accuracy score >50 (dashed horizontal line) and time score (time taken to touch the correct lighted LED panel) <30 sec (dashed vertical line). The straight line represents fit for determining correlation between accuracy score, and time score. The accuracy score and time score were found to be well correlated in low vision subjects. FIG. 9B summarizes plot of accuracy score vs. time score in better vision subjects. The dashed horizontal and vertical lines represent accuracy and time score passing criteria. As shown, all the better vision subjects were found to pass the test meeting both the accuracy and time pass criteria. FIG. 9C shows the sensitivity analysis of the Visually Guided Mobility Test in normal vision and low-vision subjects having different levels of vision. The measured Visually Guided Mobility Test score as a function of BCVA (at baseline) of eyes demonstrates that a change of 2 light level was associated with 0.3 logMAR (measured by FrACT) in individuals with severe vision loss due to RP.

Figure 10A:
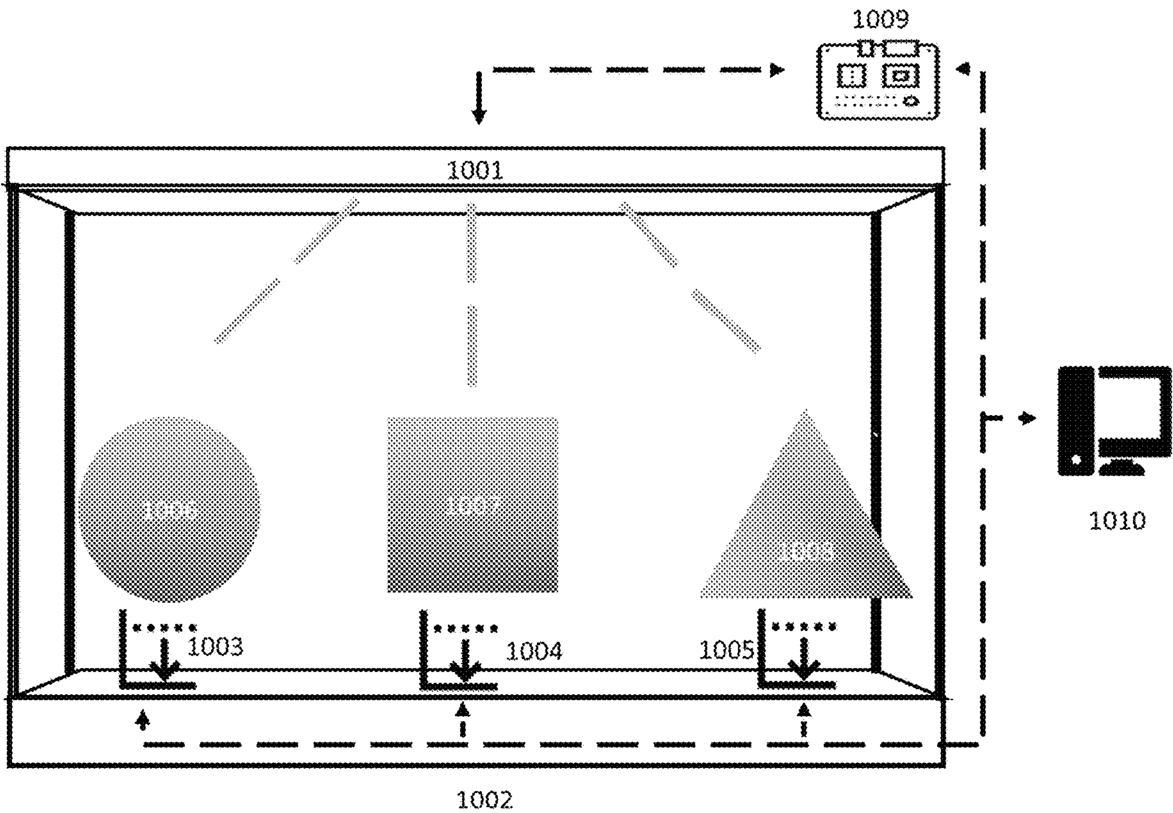
FIG. 10A. is a diagram showing a 3D Shape Discrimination Test. 1001: flat LED panel (Intensity set by user); 1002: Base of the 3D Shape Discrimination unit; 1003: Object slot 1 and pressure sensor; 1004: Object slot 2 and pressure sensor; 1005: Object slot 3 and pressure sensor: 1006: Object 1; 1007: Object 2; 1008: Object 3; 1009: Control board for adjusting LED light and communicating with pressure sensor(s). 1010: PC communicate with the control board to take inputs from the user and display which object(s) is(are) picked up based on pressure sensor.
Figure 10B:
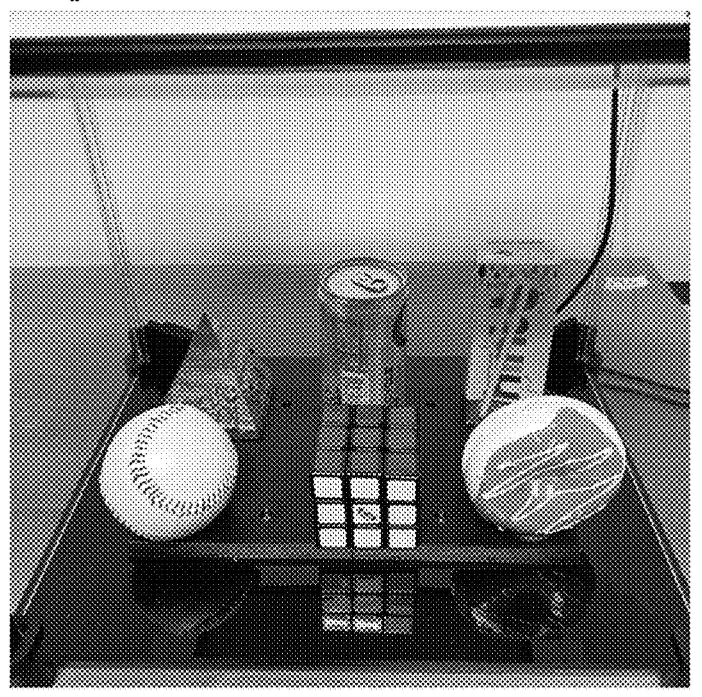
FIG. 10B. is an image of a 3D-Shape Discrimination Test set up configured with an assortment of 6 large-sized real-world objects which are equivalent to geometric shapes pyramid, donut, brick, cube, cylinder, and sphere.

Example 10: Near vision (objects within hand reach distance) of low vision subjects is evaluated via discrimination static/moving objects of varying shapes (and/or different sizes) in two-dimensional (2D) and three-dimensional (3D) configurations as well as determination direction of moving patterns (optical flow) at multiple luminance level. The 2D shape discrimination emulates a subject using smart display devices (used in daily activities such as cell phone, tablets, computers), and 3D shape discrimination of objects that are illuminated at different luminance level emulates different lighting conditions while performing activities of daily living. A normal vision or better is expected to perform all the low vision tests without difficulty. Example of 3D shape discrimination test set up is shown in FIG. 10A. The 3D shape discrimination apparatus has a flat LED panel (1001) mounted at the top of the apparatus. The LED panel is set to pre-calibrated light intensity levels to illuminate different objects (1006, 1007, 1008) placed at the base (1002) of the 3D Shape Discrimination unit. The pressure sensors (1003, 1004 and 1005) that are attached to the base of the 3D Shape Discrimination, detect change in the pressure when the objects are placed or displaced. The control board (1009) communicates with a PC/tablet (1010) to take input from the user to control the light intensity levels and provides feedback from pressure sensor to display which object(s) is(are) picked up based on pressure sensor reading. The objects in FIG. 10B are the real world objects that were used as a base to design the geometric shapes for test use. Positioned at a distance of 30 cm, provides an optimum viewing angle of approximately 11 degrees. This ensures evaluation suitability for low-vision users. To facilitate object interaction, appropriate spacing (minimum: 3 cm) between objects was maintained, allowing subjects to pick up objects without interference. The arrangement includes two rows.

Figure 11A:
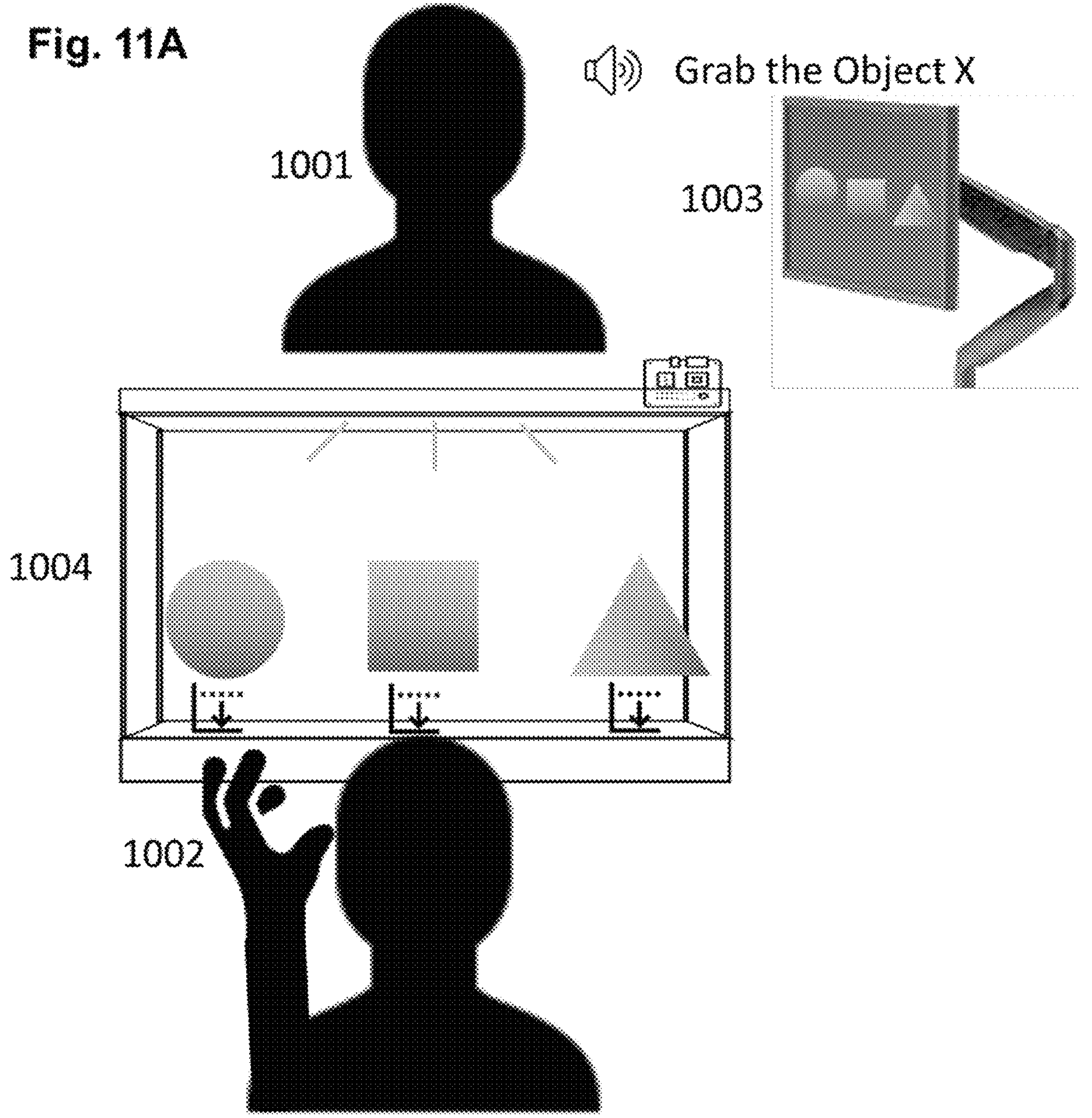
FIG. 11A. is a diagram of an Example of 3D Shape discrimination setup. Proctor (1001) of the test sits on the opposite side of the subject (1002), and the graphical user interface (GUI) is displayed in the monitor screen (1003) displaying the orders of objects need to be placed in 3D Shape Discrimination platform (1004). Once the objects are arranged on the platform, which object to be picked up is announced (by proctor according to the GUI, or by automated voice in the GUI). The test ends when the subject picks up any object regardless of correctness. Then the test is repeated in the same light level for a predetermined set of times before moving on to tests with higher illumination intensity.
Figure 11B:
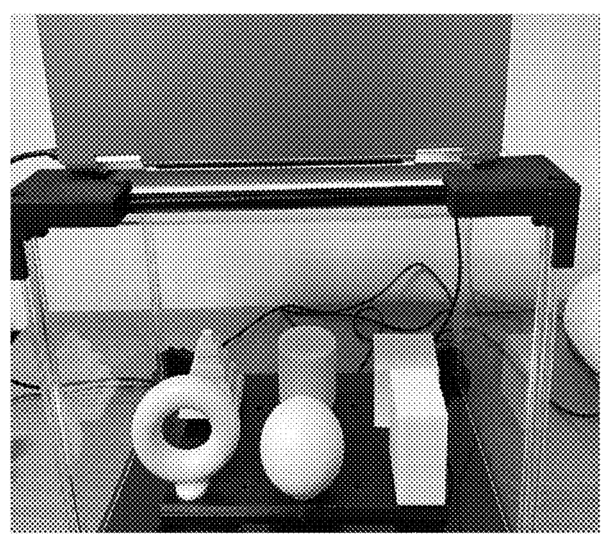
FIG. 11B. is a picture of a 3D Shape Discrimination Test set up configured with an assortment of 6 large sized-objects (pyramid, donut, brick, cube, cylinder and sphere)
Figure 11C:
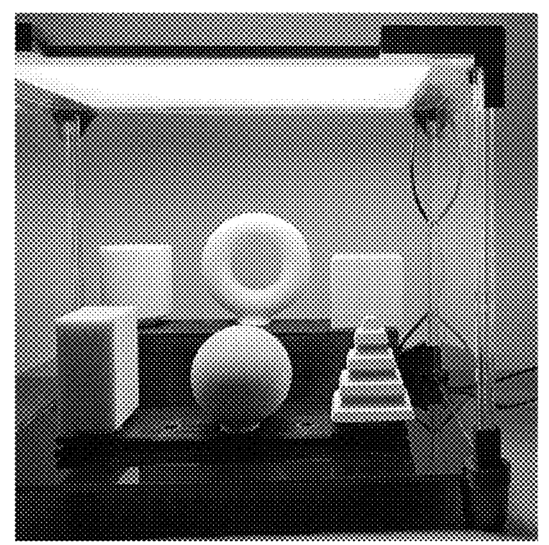
FIG. 11C. is a picture of a 3D-Shape Discrimination Test set up configured with an assortment of 6 large sized-objects (pyramid, donut, brick, cube, cylinder and sphere) in a row of two separate heights.
Figure 11D:
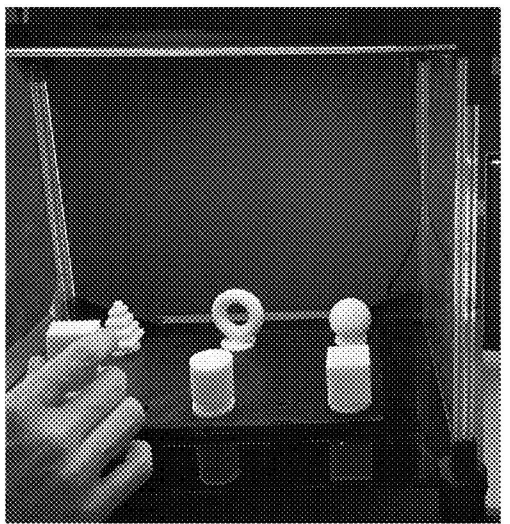
FIG. 11D. is a picture of a 3D Shape Discrimination Test set up configured with an assortment of 6 medium sized-objects (pyramid, donut, brick, cube, cylinder and sphere. Reduction of object size increases difficulty.
Figure 11E:
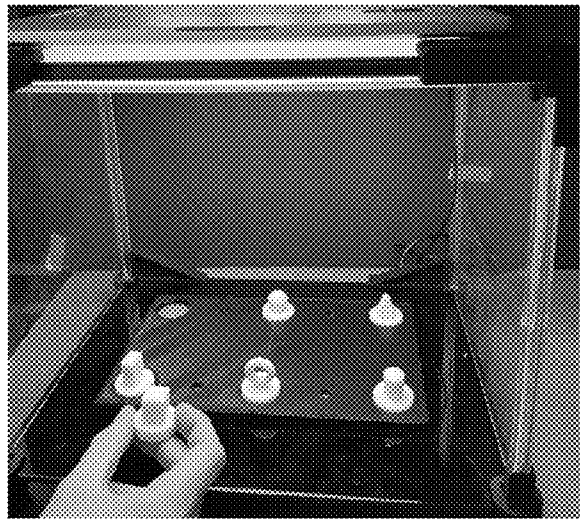
FIG. 11E. is a picture of a 3D Shape Discrimination Test set up configured with an assortment of 6 small sized-objects (pyramid, donut, brick, cube, cylinder and sphere). Reduction of object size increases difficulty.

Example 11: FIG. 11A illustrates example of 3D Shape Discrimination setup including the positions of the subject, proctor and the display. Proctor (1001) of the test sitting on the opposite side of the subject (1002) has easy access to the graphical user interface (GUI), displayed in the monitor screen (1003). The subject does not have access to the GUI and the display on the monitor screen. The display monitor light intensity is dimmed to maintain controlled low luminance (e.g., <1 lux ambient room light) level environment for the testing. The GUI displays the orders of objects such as sphere, cube and pyramid that need to be placed in the 3D Shape Discrimination platform (1004). Once the objects are arranged on the platform by the proctor, the object to be picked up is announced (by proctor according to the procedure, or by automated voice in the GUI). The pressure sensor (or camera sensor) ensures that the 3D objects are placed in correct order. The subject is instructed to pick up the object within a time cut-off, and not allowed to change his/her decision once (s)he touched an object (as the texture of the object can influence the decision). The trial concludes when the subject picks up any object regardless of correctness. The pressure sensor in the 3D Shape Discrimination apparatus provides feedback to the software and record the shape that was picked up in that trial. The test is repeated in the same light level for a preset number of times before moving on to higher illumination intensity. In the 3D Shape Discrimination, object identification and pick up by the subject emulates the activity of daily living situations such as (i) picking up fruits on the table; and (ii) picking up a glass of water. In FIG. 11B, the six geometrical objects were arranged in a three by two format to increase the number of choices available per trial and to increase difficulty. The back row will allow for objects to be stored for additional difficulty or simultaneously used as requested objects to increase the number of possible objects. In the event that only first row objects will be options it gives variability to the objects presented to the subject. To Further evaluate subjects' discrimination ability multiple heights are introduced as seen in FIG. 11C. The multiple heights introduce a variability within light reflectance that is also controlled giving 2 stages of possible difficulty within each light level. The addition of medium sized objects give rise to another measuring point of the system as seen in FIG. 11D. Reduction of size similar to reduction of font size in writing lowers visual clarity raising the difficulty on the test while maintaining scalability. FIG. 11E demonstrates the smallest size chosen to showcase the ability of the test to increase in difficulty and to extend to even those with 20/20 vision.

Figure 12D:
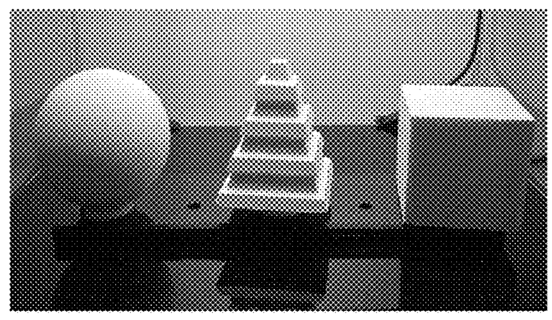
FIG. 12D. is a picture of a Set up configured with an assortment of 3 large sized-objects (pyramid, cube, and sphere) in showcasing object rotating during testing. Platform with rotation hidden beneath objects. Position 1 during rotation is shown.
Figure 12E:
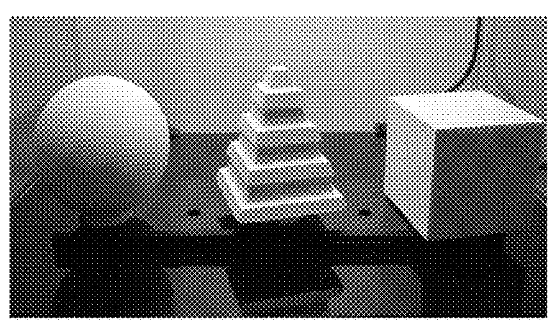
FIG. 12E. is a picture of a Set up configured with an assortment of 3 large sized-objects (pyramid, cube, and sphere) in showcasing object rotating during testing Platform with rotation hidden beneath objects. Position 2 during rotation is shown.
Figure 12F:
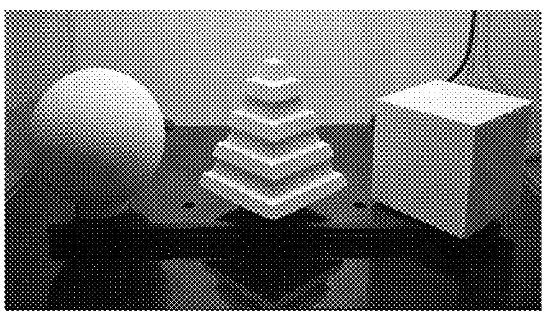
FIG. 12F. is a picture of a Set up configured with an assortment of 3 large sized-objects (pyramid, cube, and sphere) in showcasing object rotating during testing Platform with rotation hidden beneath objects. Position 3 during rotation is shown.
Figure 12G:
FIG. 12G. is a picture of a Set up configured with an assortment of 3 large sized-objects (pyramid, cube, and sphere) in showcasing object rotating during testing Platform with rotation hidden beneath objects. Position 4 during rotation is shown.

Example 12: FIG. 12A illustrates example of a 3D Shape Discrimination framework under controlled low luminance environments. The flat LED panel (with diffuser) provides uniform illumination to objects and reflections of the objects to the subject's eye. In this example, three different types of objects are placed on the base of the 3D Shape Discrimination apparatus mounted with pressure sensor. FIG. 12B demonstrates how a subject would reach the announced object and pick it up. The pressure sensor recognizes the object that is picked up and the location. Software output from the 3D Shape Discrimination assay is summarized in FIG. 12C. Light intensity (measured in lux), object position information, target shape and location, shape of object picked up by a subject, and correctness of the shape discrimination are provided. Utilizing movement FIG. 12D serves as an additional tool to enhance object silhouettes, offering an alternative detection method for low vision subjects beyond contrast enhancement. FIG. 12E demonstrates different silhouettes on a pyramid and cube FIG. 12F demonstrates different silhouettes on pyramid and cube FIG. 12G demonstrates different silhouettes on a pyramid and cube.

Example 13: For 2D Shape Discrimination, multiple types of shapes are displayed at different intensity level in a tablet touchscreen in randomized order. The intensity level is controlled by the monitor brightness while maintaining controlled low luminance level environment. The target object shape is announced by the automated voice output of the tablet speaker, and the subject is instructed to touch the target object with his/her finger as shown in FIG. 13A. The objects have different shapes and sizes, and the randomized objects are either stationary or floating as shown in FIG. 13B. After announcement of the target shape, the test ends when the subject touches the touchscreen regardless of the correctness. FIG. 13C shows correlation plot of size threshold score with best corrected visual acuity (BCVA) in two different groups of low vision patents. The test was conducted to evaluate various vision-related parameters such as size detection threshold, shape recognition ability, in low-vision patients. The objects were shaped into either circular, square, or triangular shapes. The intensities of the display were varied to determine the intensity threshold of recognizing shapes by the low-vision subjects. 2D Shape Discrimination tests revealed that the intensity threshold to detect different static shapes is different for Counting Finger vision subjects vs. subjects with hand motion vision. Further, with increase in intensity level, the shape discrimination accuracy increased significantly.

The size-threshold of 2D Shape Discrimination Test was found to be correlated with BCVA only for subjects having $<1.95$ logMAR. The poor correlation in profoundly impaired low-vision subjects (BCVA$>1.95$) is due to the inability of the subjects to detect optotypes (in Freiburg Acuity) owing to low-luminance of Freiburg Acuity measuring display device. FIG. 13D shows correlation plot of 2D Shape Discrimination accuracy with measured BCVA. The straight line represents fit for determining correlation between BCVA and 2D Shape Discrimination accuracy. The intensities of the 2D Shape Discrimination display panel was varied to determine the intensity threshold of recognizing shapes. At the threshold intensity level (22 Lux), the shape (circle, triangle and square) discrimination accuracy increased in low-vision patients with better BCVA (lower logMAR value). Software output from the 2D Shape Discrimination assay is summarized in FIG. 13E. Light intensity, shape position information, target shape and location (XY coordinates of the center of mass) of the shapes, shape of object selected by a subject, XY coordinates of the subject's touch input on the touchscreen, distance between input of the subject and center of mass of the target object coordinates, and elapsed time to touch the target object and correctness of the shape discrimination are recorded.

Example 14: The optical flow test emulates the activity of daily living situations such as (i) watching a movie on a smart device; and (ii) following moving objects (cars, people). In 2D Optical Flow test, the black and white stripes at different frequency that flow into random directions are displayed in touchscreen. FIG. 14A illustrates flow moving towards the left and FIG. 14B shows flow moving towards up (in an upwardly direction). The subject is asked to tell which direction the flow is moving or asked to touch the side of touchscreen where the flow is moving towards. FIG. 14C shows a summary of output from the 2D optical flow determination assay. Flow direction, XY coordinates of the touch input, elapsed time and correctness of the flow direction determinations are provided. Optical flow direction detection accuracy and upper speed threshold for correctly detecting optical flow was determined in low-vision patients. Laterally or radially moving (inward or outward) vs. stationary illumination patterns were displayed, and the subject were asked to recognize the optical flow. Testing was performed monocularly in counterbalanced order. The upper speed threshold (to accurately detect direction of optical flow) was found to be dependent on visual acuity. Further, with increase in the display intensity level, the shape discrimination accuracy increased significantly.

Figure 15A:
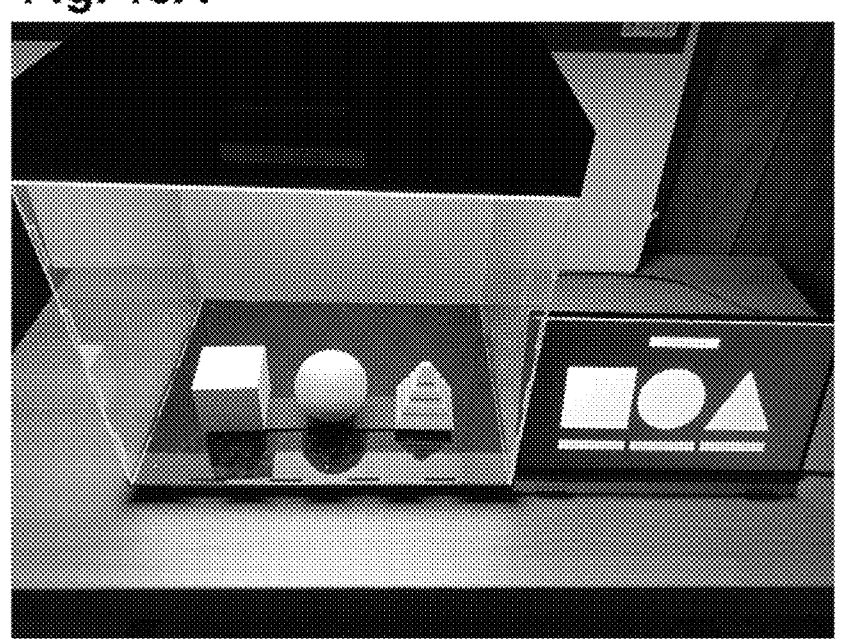
FIG. 15A. is a picture of a 3D and 2D Shape Discrimination setup.
Figure 15B:
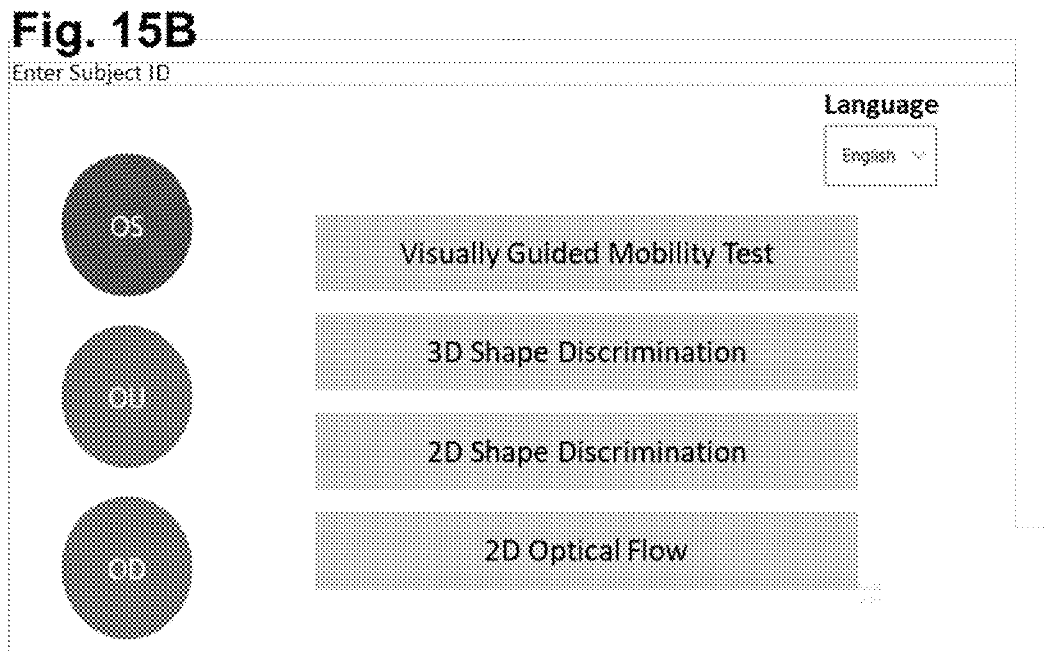
FIG. 15B. is an image of a Graphical user interface for 2D/3D shape recognition and optical flow test.

Example 15: FIG. 15A shows 3D Shape Discrimination and 2D Shape Discrimination apparatus under low illumination environment. Both devices are connected to a single control device (PC/laptop/tablet). The software interface for tests including 2D/3D Shape Discrimination and Optical Flow is shown in FIG. 15B. The low vision test systems are portable having small form factor and imitates real life interactions to correlate the visual functions to quantitative measurements in low vision subjects.

Figure 16A:
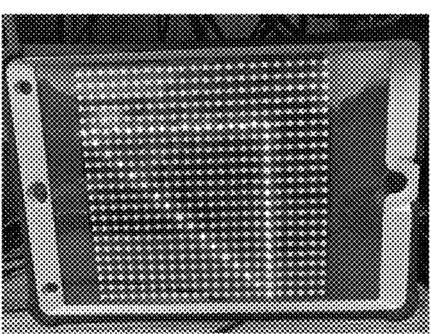
FIG. 16A. is an image of a Triangle shape displayed in the LED panel.
Figure 16B:
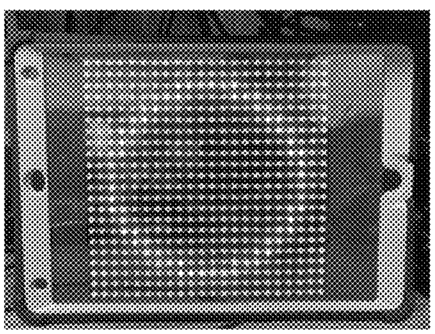
FIG. 16B. is an image of a Circle shape displayed in the LED panel.
Figure 16C:
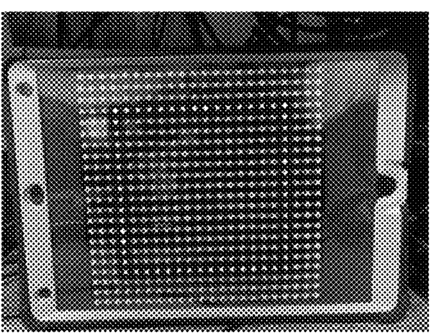
FIG. 16C. is an image of a Square shape displayed in the LED panel.
Figure 16D:
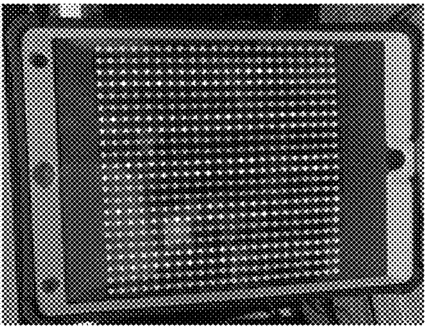
FIG. 16D. is an image of a Optical flow pattern displayed in the LED panel.
Figure 16E:
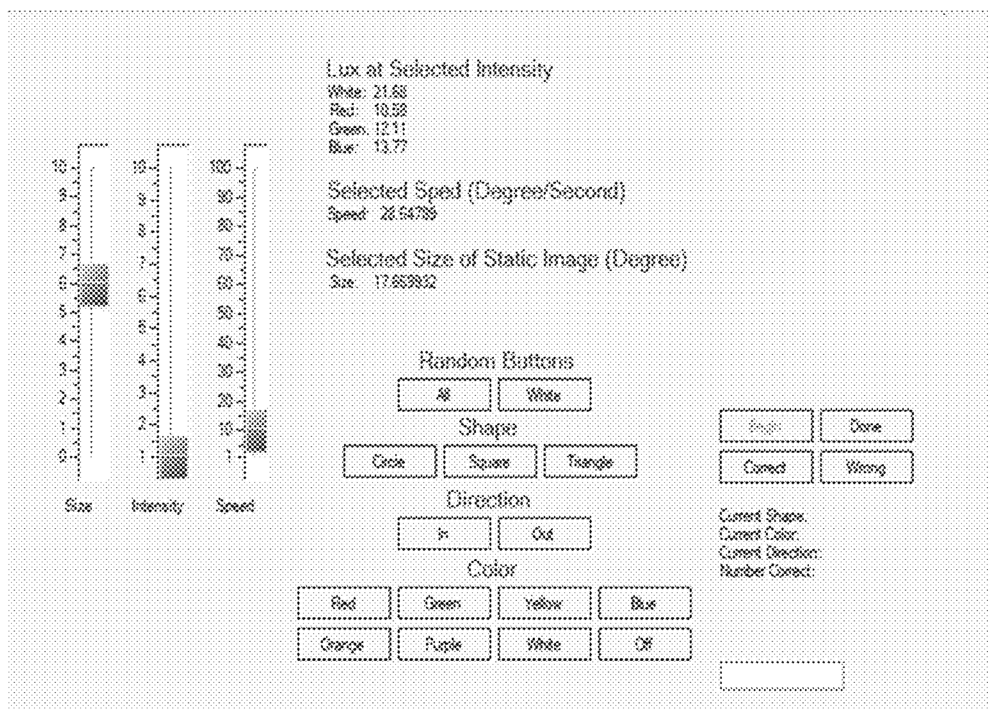
FIG. 16E. displays a Graphical user interface for LED based 2D Shape recognition, and optical flow. Multiple display parameters such as intensity, shape, color, and size of the objects, and direction and speed which objects and optical flows are provided.
Figure 16F:
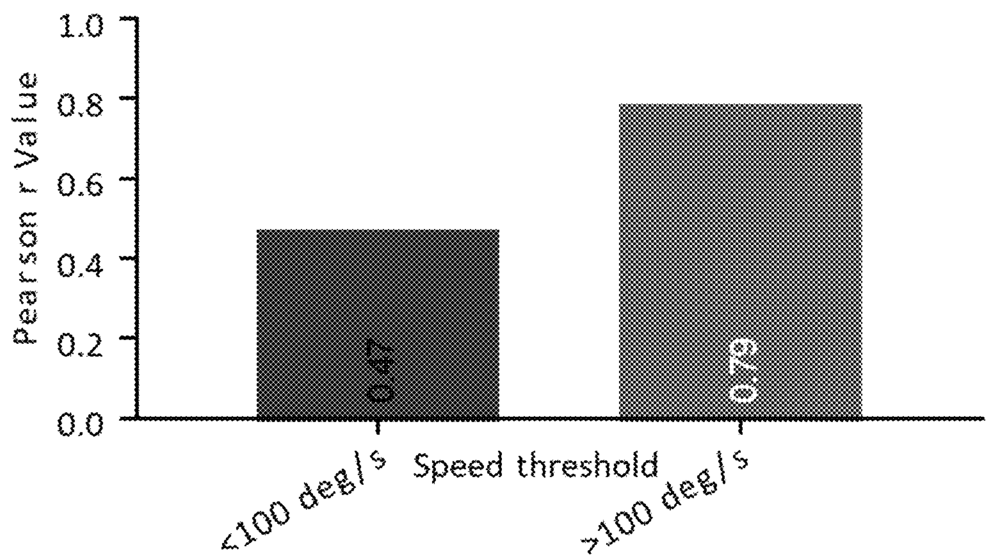
FIG. 16F. is a graph showing the Association speed threshold of Optical Flow with Patient Reported Outcome (PRO, measured by NEI-VFQ) in Low-Vision patients. Pearson Correlation between speed threshold and PRO for two different groups.

Example 16: FIG. 16A shows an image of a triangle displayed on the 2D Shape Discrimination apparatus using LED arrays. Arrays exhibiting various 2D shapes with different colors along with stripes (for optical flow test) are displayed. Circle Displayed in FIG. 16B. Square Displayed in FIG. 16C. Optical flow pattern displayed in FIG. 16D. FIG. 16E shows the Graphical user interface for LED-array based 2D Shape recognition, and optical flow test. Control for multiple display parameters such as intensity, shape, color, and size of the objects, as well as direction and speed of optical flows are provided in the GUI. FIG. 16F shows association of a measured speed threshold of Optical Flow with Patient Reported Outcome (measured by NEI-VFQ) in Low-Vision patients. Pearson Correlation between speed threshold and PRO for two different groups.

The specification and examples herein provide a complete description of the structure and use of illustrative embodiments. Although certain embodiments have been described with a certain degree of particularity, or with reference to one or more individual embodiments, those skilled in the art could make numerous alterations to the disclosed embodiments without departing from the scope of this invention. As such, the various illustrative embodiments of the devices are not intended to be limited to the particular forms disclosed. Rather, they include all modifications and alternatives falling within the scope of the claims, and embodiments other than the one shown may include some or all of the features of the depicted embodiment. For example, components may be omitted or combined as a unitary structure, and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

While the device, and methods of this invention have been described in terms of preferred embodiments, it will be apparent to those of skill in the art that variations may be applied to the device, and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the present invention.

Furthermore, the claims are not intended to include, and should not be interpreted to include, means-plus- or step-plus-function limitations, unless such a limitation is explicitly recited in a given claim using the phrase(s) "means for" or "step for," respectively.

REFERENCES

The following references, to the extent that they provide exemplary procedural or other details supplementary to those set forth above, are specifically incorporated herein by reference.

ADDIN EN.REFLIST 1 Stanescu, B. & Michiels, J. Electroretinography and temporal aspects in macular dystrophy. *Ophthalmologica* 172, 367-378, doi:10.1159/000307736 (1976).

2 Birch, M. K., Wishart, P. K. & O'Donnell, N. P. Determining progressive visual field loss in serial Humphrey visual fields. *Ophthalmology* 102, 1227-1234; discussion 1234-1225, doi:10.1016/s0161-6420(95)30885-8 (1995).

3 Hartong, D. T., Berson, E. L. & Dryja, T. P. Retinitis pigmentosa. *The Lancet* 368, 1795-1809 (2006).

4 Birch, D. G., Anderson, J. L. & Fish, G. E. Yearly rates of rod and cone functional loss in retinitis pigmentosa and cone-rod dystrophy. *Ophthalmology* 106, 258-268, doi:10.1016/S0161-6420(99)90064-7 (1999).

5 Rice, T. A. The early treatment diabetic retinopathy study. *Trans Pa Acad Ophthalmol Otolaryngol* 35, 24-30 (1982).

6 Bach, M. [The Freiburg Vision Test. Automated determination of visual acuity]. *Ophthalmologe* 92, 174-178 (1995).

7 Chung, D. C. et al. Novel mobility test to assess functional vision in patients with inherited retinal dystrophies. *Clinical & experimental ophthalmology* 46, 247-259 (2018).

What is claimed is:

1. A method of evaluating functional vision in low vision subjects comprising at least one of the steps selected from:

(i) conducting a Visually Guided Mobility Test comprising a single or multiple Light panel(s) for emitting light at different intensity levels; providing a single or multiple randomly-selected starting point(s) for a subject to find at least one of the Light panel(s) that is emitting light or a lighted object; providing a variable number of obstacle(s) positioned at different locations in the path to the Light panel(s) or the lighted object(s) to assess the ability of the subject to avoid them; providing video camera(s) for recording the mobility of the subject; providing a computer for switching at least one of the Light panel(s) or light shining on the object(s) ON/OFF, and varying the Light panel(s) light intensity or intensity of light shining on the object(s) and color by integrated software for directing and recording the performance of the Visually Guided Mobility Test; wherein the ability of the subject to detect and freely navigate towards the Light panel(s) that is emitting light or lighted object(s) and avoid the obstacles is evaluated, without any other visual cues for direction;

(ii) conducting a Visually guided Dexterity Test comprising a pre-calibrated Light panel for controlled illumination; providing differently shaped Three-dimensional (3D) objects that are stationary or moving; lighting the objects by the Light panel; detecting when the objects are placed or displaced; providing a control board communicating with a computer for controlling the light intensity levels of the Light panel; providing integrated software for providing instructions to the subject in a randomized order and for recording the performance of the subject; wherein the Visually guided Dexterity Test evaluates the ability of a subject to detect and discriminate an object and/or motion from a collection of differently sized/shaped/colored stationary/moving objects for near vision evaluation in three-dimensions; and/or (iii) conducting a Visually Guided Dexterity Test comprising multiple types of shapes being displayed at different intensity levels on a screen or Light panel in randomized order, wherein the Visually Guided Dexterity Test evaluates the ability of a subject to discriminate 2D objects of different sizes/shapes displayed at pre-allocated random locations on the screen or Light panel; or conducting the Visually Guided Dexterity Test with the screen or Light panel displaying light and dark moving stripes/rings of different frequencies and intensities; and evaluating the ability of the subject to detect the direction of motion of the pattern; and evaluating functional vision based on success of the completion of a task based on the accuracy of the mobility and dexterity tasks including (i) touching the Light panel while avoiding the obstacles, (ii) touching/picking up the target object, and/or detecting correct direction of motion.

2. The method of claim 1, wherein the subject has normal vision, or visual impairment in one or both eyes.

3. The method of claim 1, comprising evaluating the functional vision of at least one eye of the subject.

4. The method of claim 1, wherein the subject previously received or is expected to receive ocular therapy or surgery in one or both eyes.

5. The method of claim 1, the method being for assessing the functional vision quantitatively in multiple light intensity levels in subjects with low vision.

6. The method of claim 1, wherein the Light panel(s) or the light shining on object(s) provides varying light intensities ranging from 0.1 lux to 100 lux for evaluation of real-life visually guided mobility and/or dexterity vision in rod driven and cone driven conditions.

7. The method of claim 1, comprising assessing the individual S, M or L cone based functional vision by varying the color of light emitted by the Light panel.

8. The method of claim 1, comprising evaluating the change in functional vision by scoring the subject's visually guided mobility and dexterity test performance at varying light intensities, with a highest score for passing the test at lowest light intensity and lowest score for not passing the test at highest light intensity.

9. The method of claim 1, comprising using multiple Light panels or starting positions, increasing number of obstacles or objects, and/or randomizing the positioning of the objects, obstacles, and subject to minimize a learning effect of the subject while performing the visually guided mobility and dexterity tests.

10. The method of claim 1, comprising adjusting the difficulty level of the visually guided mobility and dexterity tests to evaluate subjects with a specific or broad range of ocular diseases based on their functional vision status.

11. An apparatus configured for performing functional vision tests in low vision subjects comprising: a single or multiple Light panel(s) for emitting light or shining light on object(s) at different intensity levels; a single or multiple randomly-selected starting point(s) for a subject to find at least one of the Light panel(s) that is emitting light or the light shining on object(s); a variable number of obstacle(s) positioned at different locations in the path to the Light panel(s) or the light shining on object(s); a video camera for recording the mobility of the subject; a computer for switching at least one of the Light panel(s) ON/OFF, and integrated software operable to vary the light intensity and color of the Light panel(s), wherein the size, shape, and number of Light panels or the light shining on object(s) is selectable;

wherein the Light panel(s) or the light shining on object(s) comprises an LED display operable to generate specific frequency of LED patterns;

wherein the distance between adjacent Light panel(s) or lighted object(s), and distance between the starting point to the Light panel(s) or the lighted object(s) is selectable;

wherein control of dynamic range of light intensity from the at least one Light panel(s) or the light shining on object(s) is adjustable;

wherein the position of the single or multiple obstacle(s) between the starting point and the at least one Light panel(s) or the light shining on object(s) is adjustable; and a control module for providing instructions to the subject;

wherein the apparatus is configured for evaluating functional vision based on success of the completion of a task based on the accuracy of mobility and dexterity tasks including (i) touching the Light panel(s) while avoiding obstacles, (ii) touching/picking up a target object, and/or detecting correct direction of motion.

12. The apparatus of claim 11 configured for functional vision tests in low vision subjects comprising: a pre-calibrated Light panel for controlled illumination; differently shaped Three-dimensional (3D) objects positioned at the stationary or moving portion of the apparatus; a pressure sensor(s) attached to the apparatus to detect change in the pressure when the objects are placed or displaced; a control board operable to communicate with a computer for controlling the light intensity levels of the Light panel and for reading the pressure sensor(s); integrated software for providing instructions to the subject in randomized order and for recording the performance of test, wherein the size, shape, weight and color of the objects is selectable;

wherein the objects are placed in single or multiple rows;

wherein the rows are at same height or at different heights;

wherein the objects are stationary or moving;

wherein the path and speed of moving objects is selectable;

wherein the distance between adjacent objects, and distance between the mounted Light panel and objects is selectable;

wherein the size, shape of Light panel is selectable;

wherein control of dynamic range of light intensity from the LED panel is adjustable; and a control module for providing instructions to the subject.

13. The apparatus of claim 11 for functional vision tests in low vision subjects comprising: multiple types of objects that are displayed at different intensity levels against a background on a screen or Light panel in randomized order, wherein the intensity and color of the objects and background is adjustable;

wherein the objects displayed are stationary or floating within the screen or Light panel; and wherein a touch sensor on the screen or Light panel records the screen touch by the subject for analysis.

14. The apparatus of claim 11 for functional vision tests in low vision subjects comprising: light and dark moving stripes/rings of different frequencies and intensities that are displayed on a screen or Light panel in a randomized direction, wherein the intensity and color of the light and dark moving stripes/rings is adjustable;

wherein the speed of the light and dark moving stripes/rings is adjustable; and wherein a touch sensor on the screen or Light panel records the screen touch by the subject for analysis.

* * * * *